US007989004B2

(12) United States Patent
Rathod et al.

(10) Patent No.: US 7,989,004 B2
(45) Date of Patent: Aug. 2, 2011

(54) ANTITUBERCULAR EXTRACTS OF SALICORNIA BRACHIATA

(75) Inventors: Meena Rajnikant Rathod, Gujarat (IN); Bhupendra Dhanvantrai Shethia, Gujarat (IN); Jayant Batukral Pandya, Gujarat (IN); Pushpito Kumar Ghosh, Gujarat (IN); Prakash Jagivanbhal Dodia, Gujarat (IN); Brahm S. Srivastava, Uttar Pradesh (IN); Ranjana Srivastava, Uttar Pradesh (IN); Anil Srivastava, Uttar Pradesh (IN); Vinita Chaturvedi, Andhra Pradesh (IN); Mariappanadar Vairamani, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/337,081

(22) Filed: Jan. 23, 2006

(65) Prior Publication Data
US 2007/0020351 A1    Jan. 25, 2007

Related U.S. Application Data

(63) Continuation of application No. 11/138,674, filed on May 27, 2005, now abandoned.

(30) Foreign Application Priority Data

May 28, 2004 (IN) .................................... 969/2004

(51) Int. Cl.
A61K 36/00 (2006.01)
(52) U.S. Cl. .................... 424/725; 424/773; 514/924
(58) Field of Classification Search .................. None
See application file for complete search history.

(56) References Cited

U.S. PATENT DOCUMENTS

| 2005/0186291 | A1 | 8/2005 | Rathod et al. |
| 2007/0020351 | A1 | 1/2007 | Rathod et al. |

FOREIGN PATENT DOCUMENTS

| CN | 1242991 | * | 2/2000 |
| DE | 19630323 C1 | | 8/1997 |
| FR | 2657011 | | 7/1991 |
| KR | 2002003173 | * | 1/2002 |
| WO | 03/079817 A1 | | 10/2003 |

OTHER PUBLICATIONS

Lee et al., Chemical preoperties and immunoogical activities of hot-water extract from leaves of Saltwort. Food Sci. Biotechnol. 13 (2): 167-171, 2004.*
Bhosale et al., Antifungal activity of some marine organisms from India, against food spoilage *Aspergillus* strains. Mycopathologia 147: 133-138, 1999.*
Bhosale et al, Antifungal activity of some marine organisms from India, against food spoilage *Aspergillus* strains, Mycopathologia 147: 133-138, 1999.*
Revilla et al., Comparison of several procedures used for the extraction of anthocyanins from red grapes, J. Agric. Food Chem. 46: 4592-4597, 1998.*
Williams, Fractions of methanol extracts of *Tubercle bacilli*. II. Toxic and allergenic properties of fractions employed as antituberculous vaccine, Journal of Experimental Medicine (1960), 111, 369-86.*
Anwar et al. "Analytical characterization of *Salicornia bigelovii* seed oil cultivated in Pakistan" J. Agric. Food Chem. 50:4210-4214 (2002).
Bhosale et al. "Antifungal activity of some marine organisms from India, against food spoilage *Aspergillus* Strains" Mycopathol. 147:133-138 (1999).
Bhosale et al. "Antifouling potential of some marine organisms from India against species of *Bacillus* and *Pseudomonas*" Mar. Biotechnol. 4:111-118 (2002).
Dave et al. "Effect herbal antifungal agents on 33 *Trichophyton* isolates" Proc. Nat. Acad. Sci. India 71:149-155 (2001).
Faulds et al. "A major component of cell walls, ferulic acid, influences feruloyl esterase production in *Aspergillus niger*" Biochem. Soc. Trans. 24:386S (1996).
http://web.archive.org/web/*/http://www.public.iastate.edu/~bot. 512/lectures/development&homones_512.pdf 7 pages (2005).
http://en.wikipedia.org/wiki/chloroform, four pages (2005).
http://www.ibiblio.org/pfaf/cgi-bin/arr_html?salicornia+europaea, six pages (2005).
http://www.m-w.com/cgi-bin/dictionary?book=dictionary &va=bioactive, one page (2005).
http://www.naturalfoodsmerchandiser.com/ASP/802/display-article, four pages (2005).
http://people.westminstercollege.edu/faculty/tharrison/gslplaya99/picleweed.htm, seven pages (2005).
Jang, XP002278325 of KR 20030022134 English abstract only (2003).
Khan et al. "Effect of salinity on the growth and ion content of *Salicornia rubra*" Commun. Soil Sci. Plant Anal. 32:2965-2977 (2001).
Michaud "At ORNL the emphasis is on pollution prevention" Lockheed Martin Energy Systems, Oak Ridge National Laboratory, ten pages (1996).
Pennings et al. "Feeding preferences of a generalist salt-marsh crab: Relative importance of multiple plant traits" Ecol. 79:1968-1979 (1998).
Renard et al. "Cell wall phenolics and polysaccharides in different tissues of quinoa (*Chenopodium quinoa* willd)" J. Sci. Food Agr. 79:2029-2034 (1999).
Schwartzkopf "Potassium, calcium, magnesium—How they relate to plant growth" USGA Green Section Record pp. 1-2 (1972).
Siska et al. "Latitudinal variation in palatability of salt-marsh plants: Which traits are responsible?" Ecol. 83:3369-3381 (2002).
Thangam et al. "Mosquito larvicidal activity of mangrove plant extracts and synergistic activity of *Rhizophora apiculata* with pyrethrum against culex quinquefasciatus" Int. J. Pharma. 35:69-71 (1997).

* cited by examiner

*Primary Examiner* — Qiuwen Mi
(74) *Attorney, Agent, or Firm* — Nixon & Vanderhye P.C.

(57) ABSTRACT

The present invention relates to enhancement of anti-tubercular activity of active fraction isolated from *Salicornia brachiata*. The invention also discloses the non-toxic nature of the fraction and positively identifies Sucrose as its main constituent. Pure Sucrose is shown to have no anti-tubercular activity indicating thereby that activity of the fraction resides in one or more of the minor constituents. The minor constituents are shown to be relatively low molecular weight entities and a chromatographic technique is disclosed for separating them from the bulk sucrose to probe their activities and structures in detail, as also the possibility of their synthesis if the leads thrown up are novel.

31 Claims, 19 Drawing Sheets

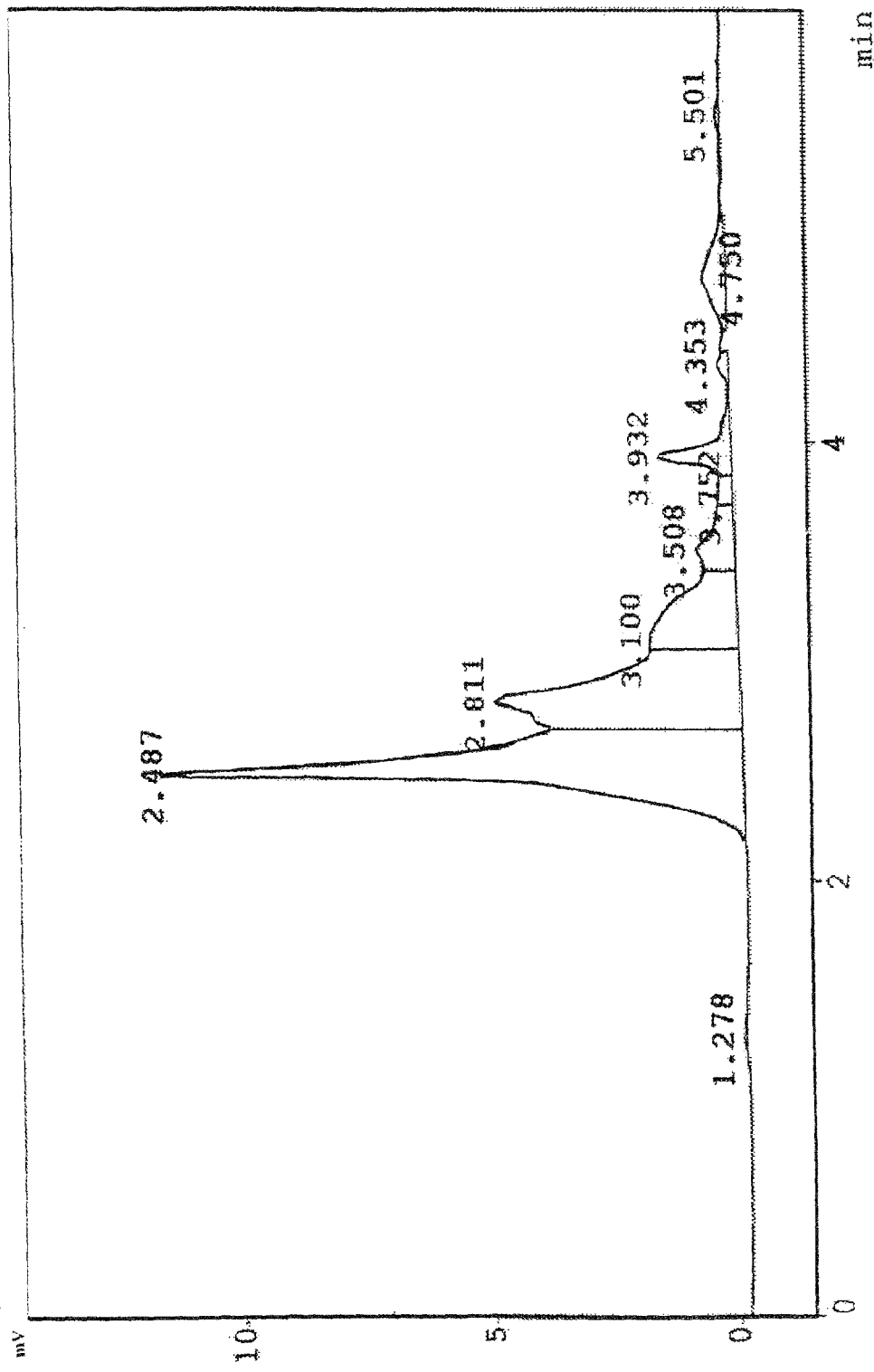
Figure. 1 of Example 1
HPLC Profile of Fraction F-2 at 254 nm.

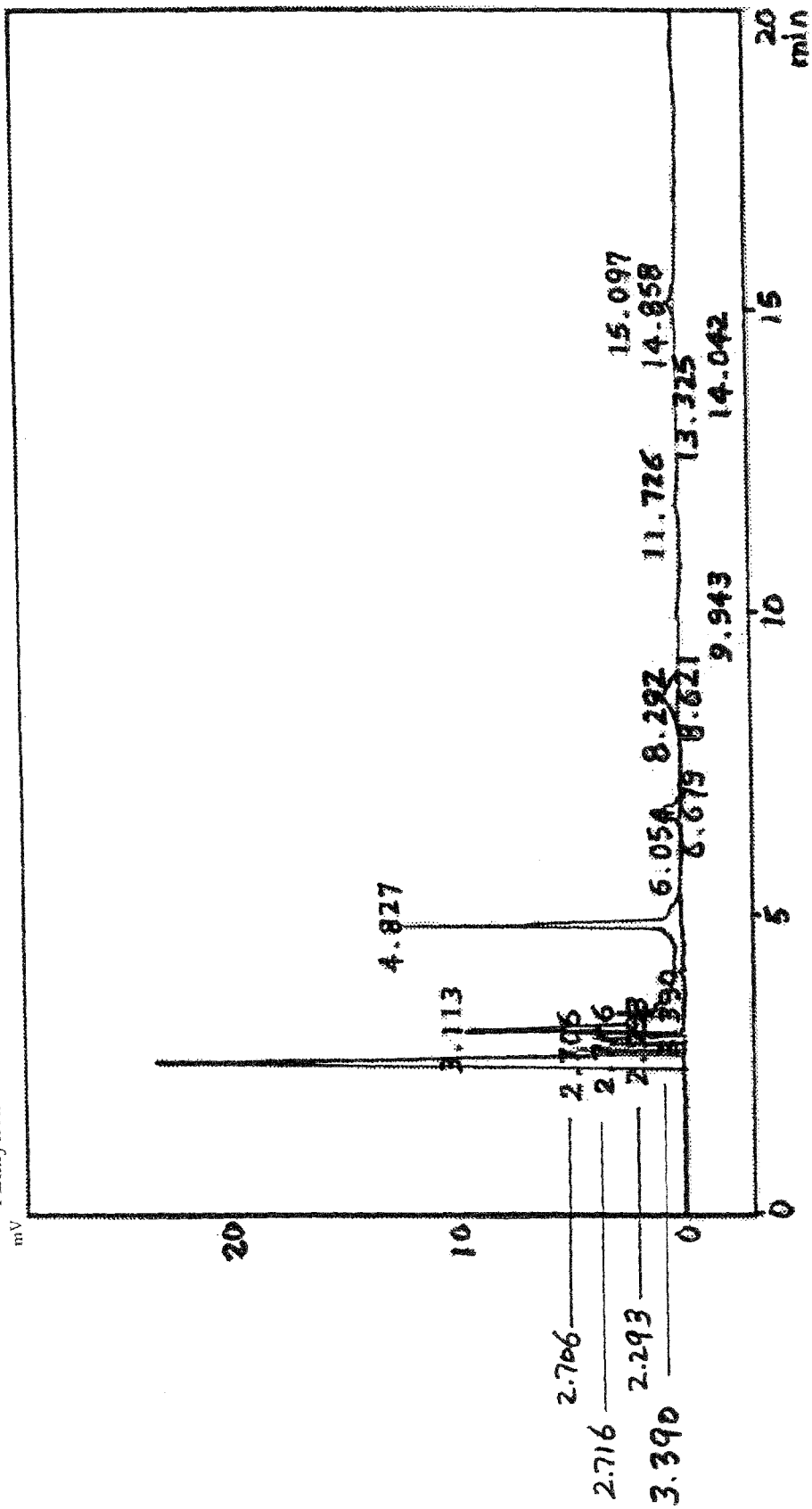
Figure: 2 of Example 1
Analytical HPLC Profile of Fraction F2 at 220 nm.

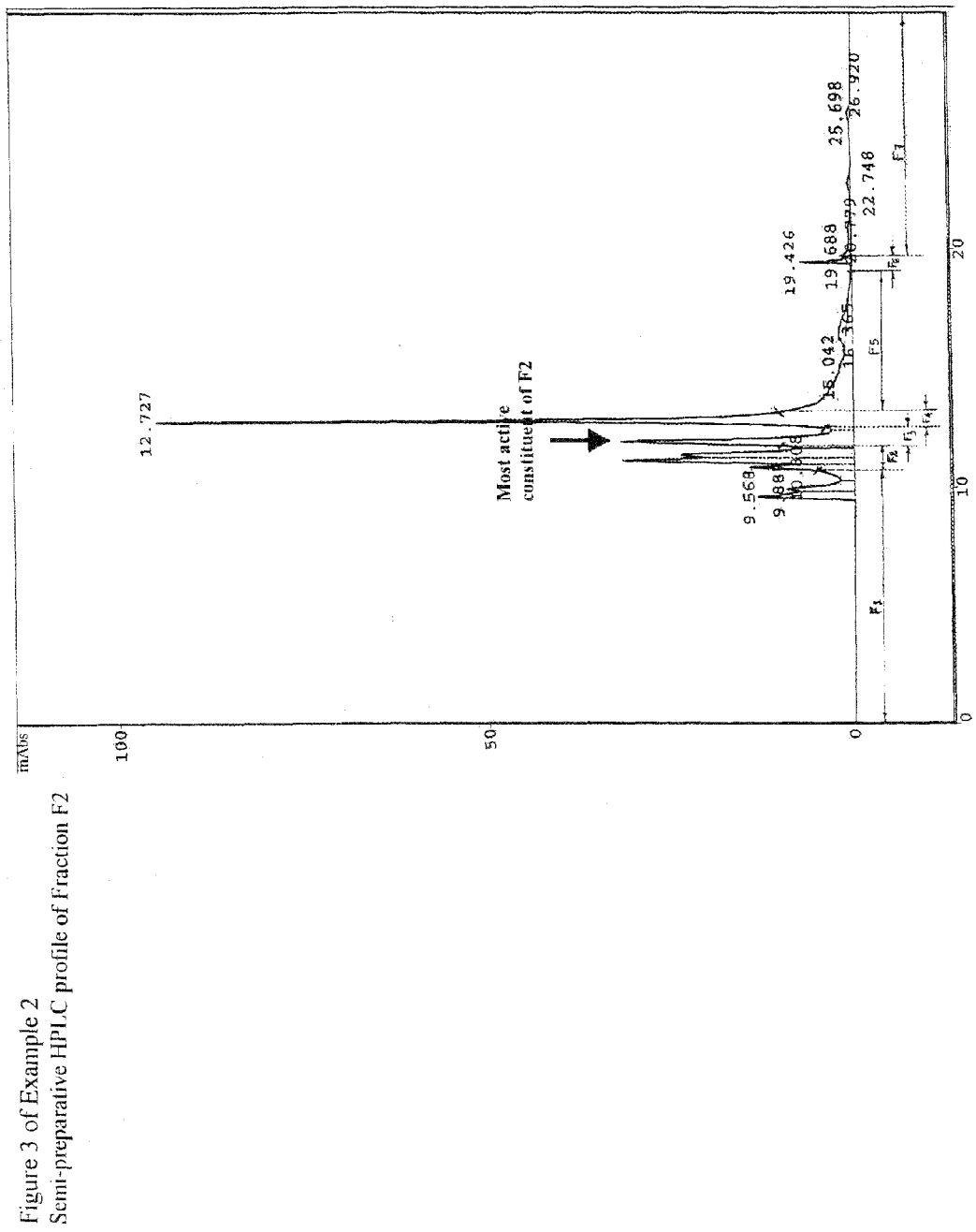
Figure 3 of Example 2
Semi-preparative HPLC profile of Fraction F2

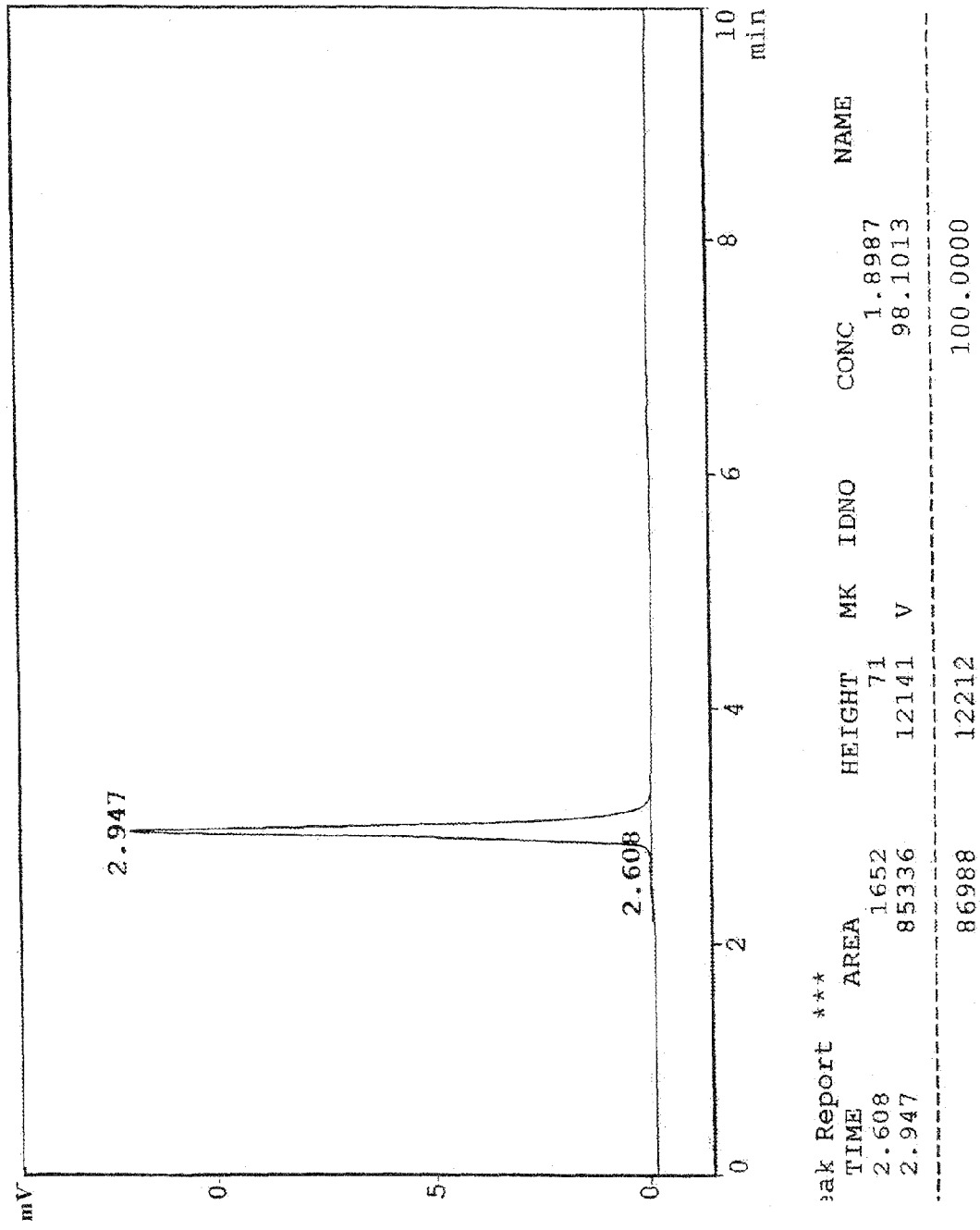

Figure: 5 of Example 8
Protection by SF3-K given orally at the dose of 50 mg./Kg. for 12 days in mice against infection of M.tuberculosis H37Rv
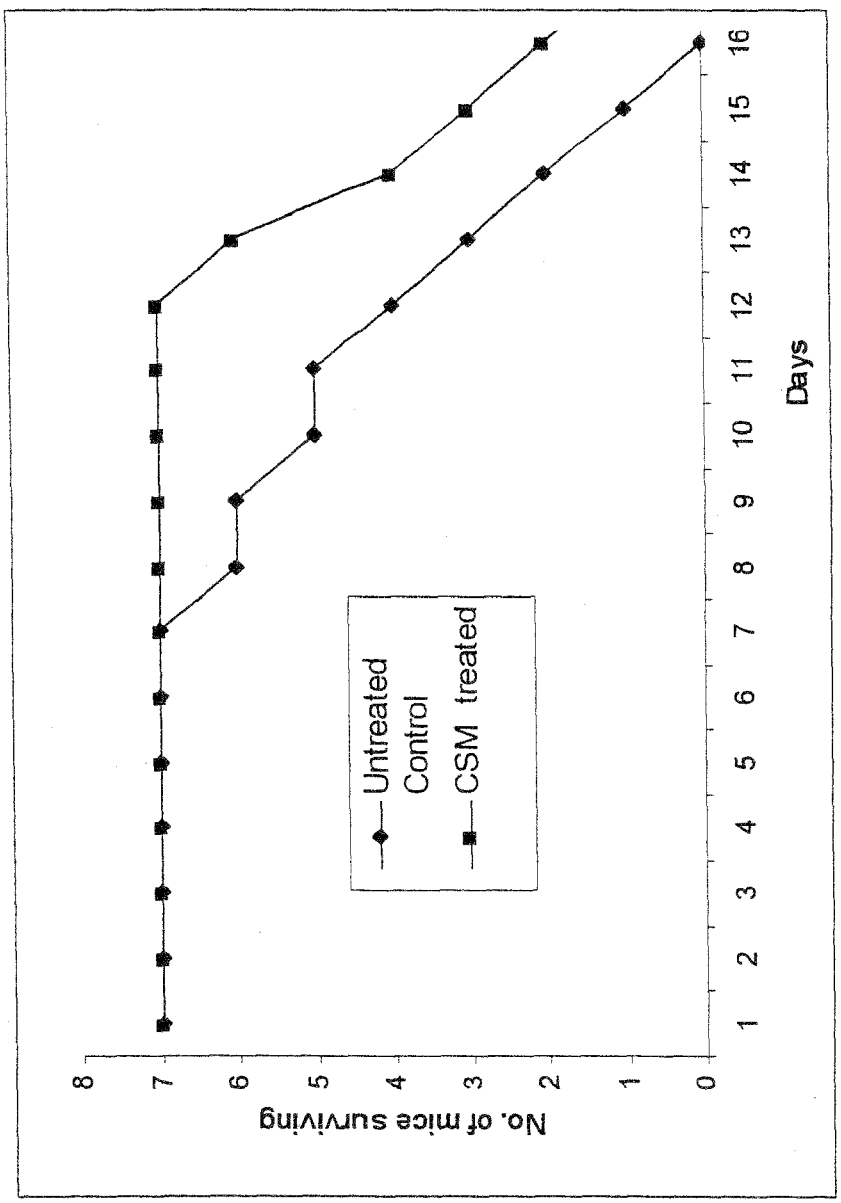

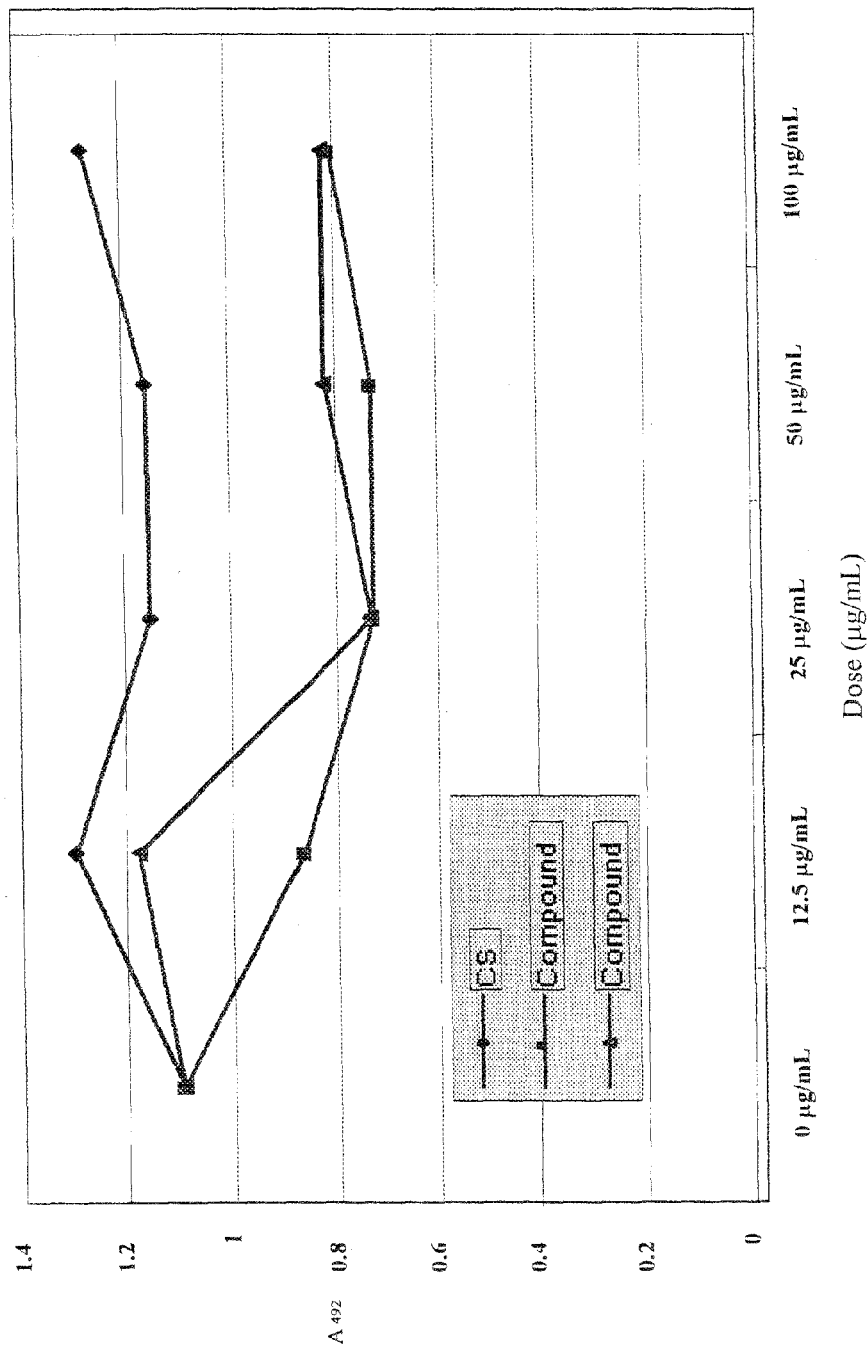
Figure 6 of Example 9
Anti-proliferative effect of SF3-K and two other coded compounds (X,Y) on VERO-C 1008 using MTT assay

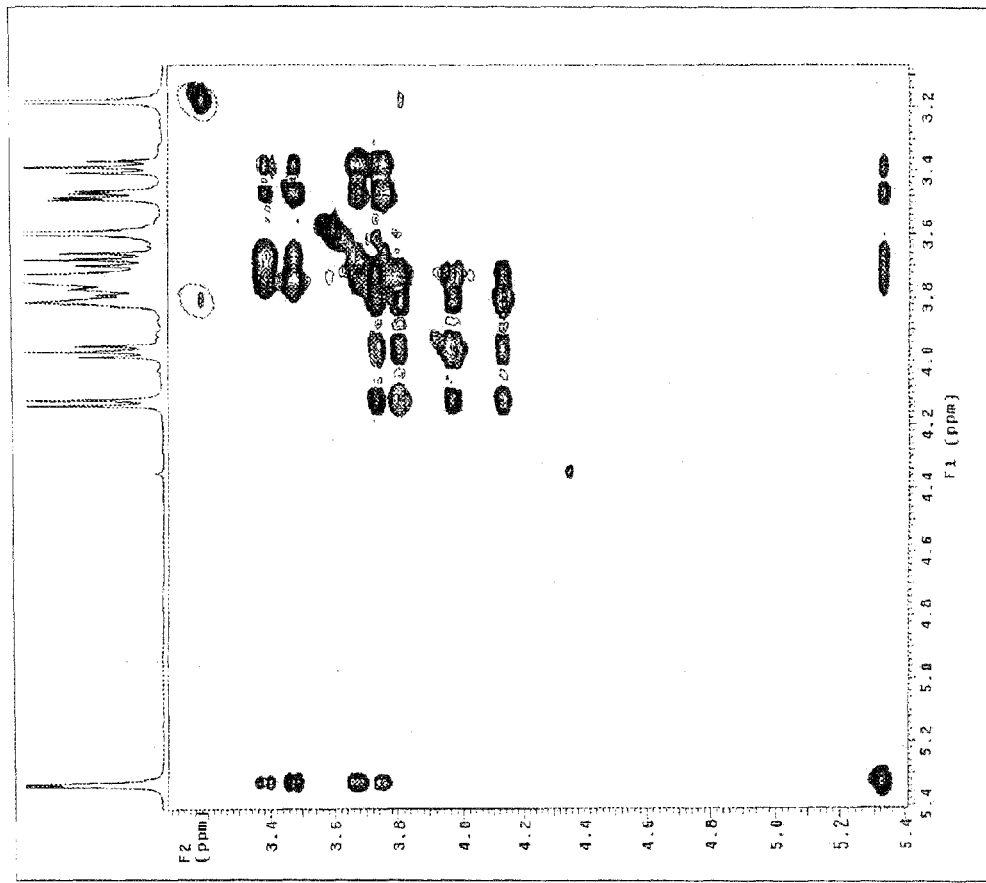
Figure: 7 of Example 11
TOCSY Spectrum of SF3-K

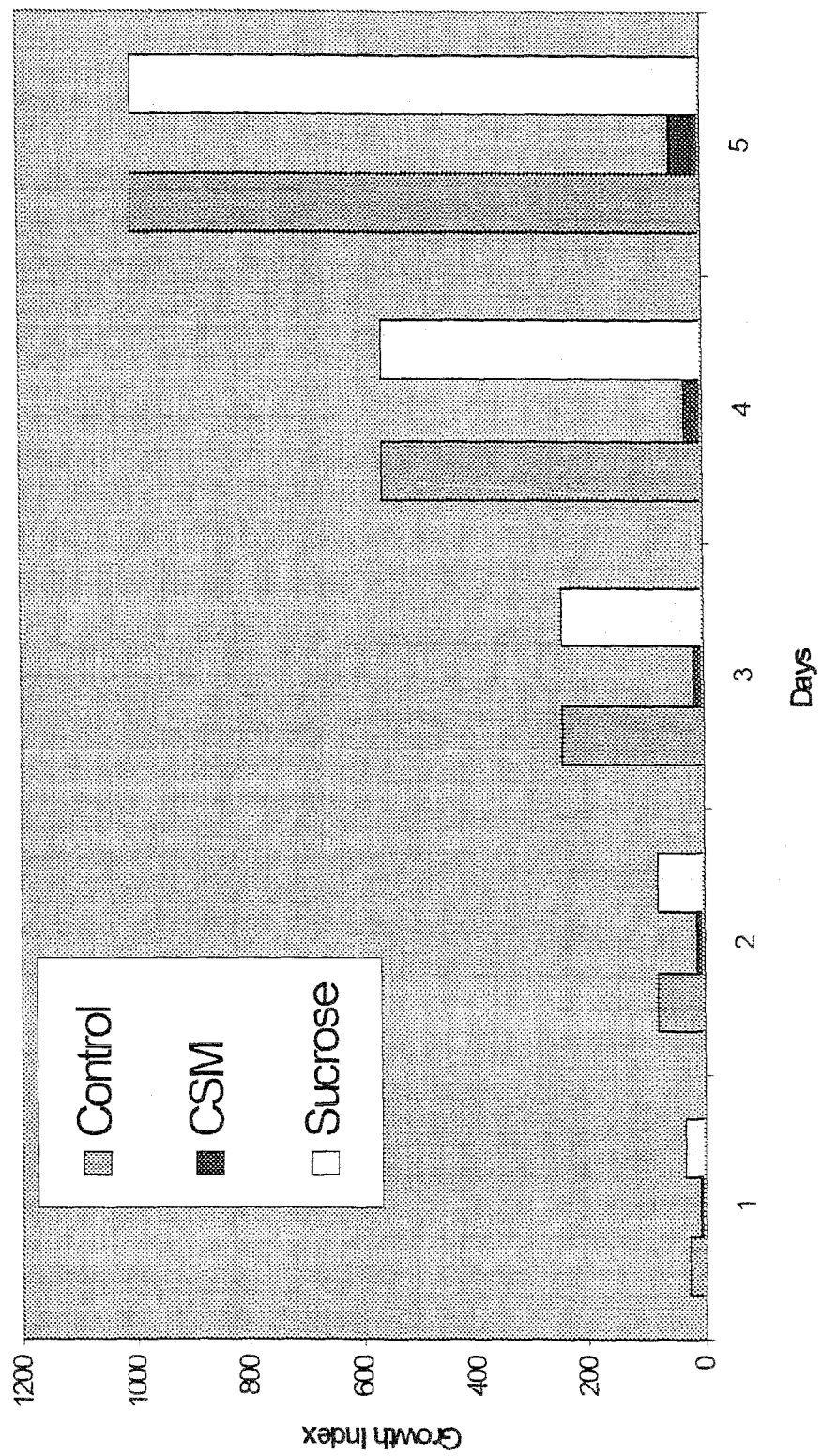
Figure: 8 of Example 12
Inhibition of growth of M.tuberculosis H37Rv by SF3-K in BACTEC

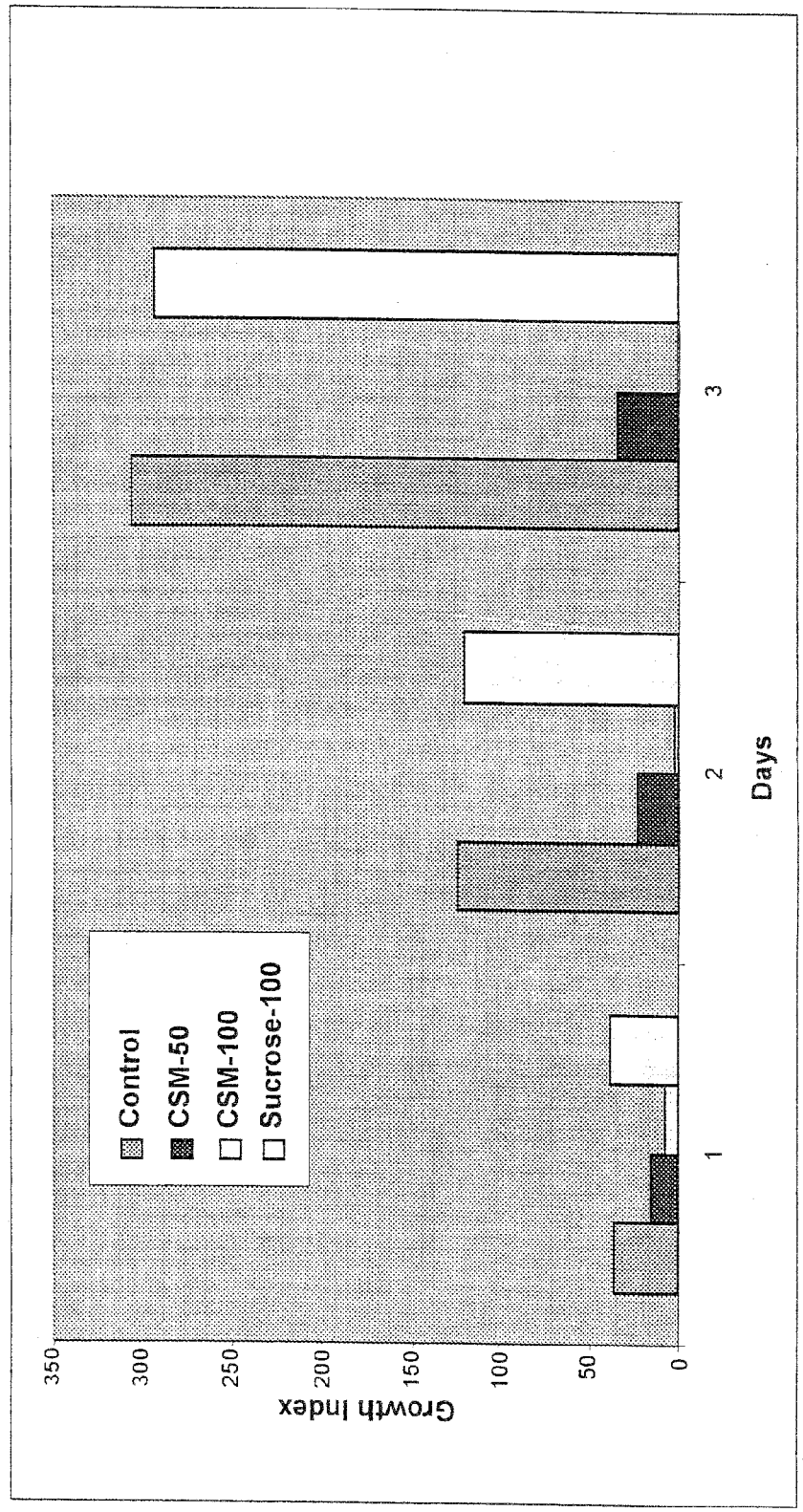
Figure: 9 of Example 13
Repeat experiment: Inhibition of growth of M.tuberculosis H37Rv by SF3-K at 50 and 100 µg./mL conc. in BACTEC.

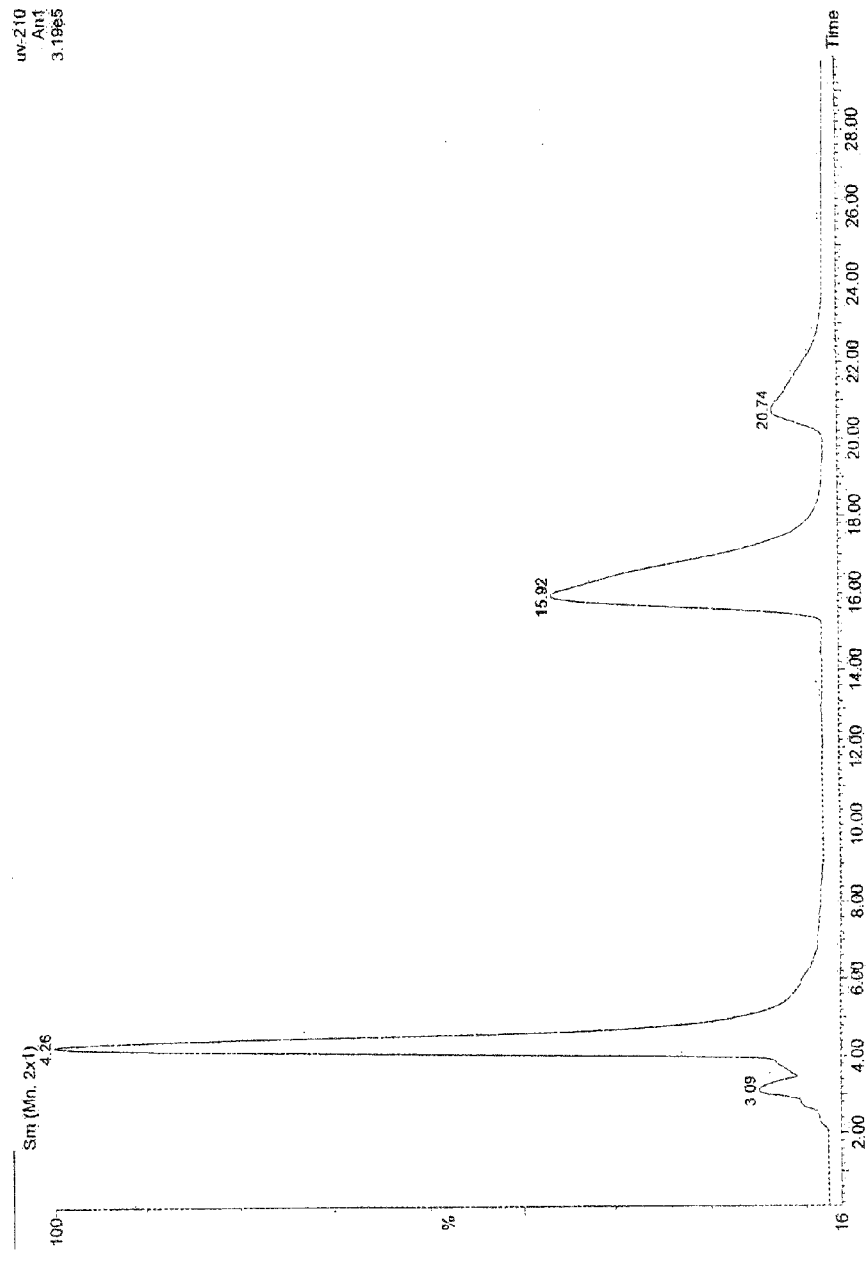
Figure: 10 of Example 15
HPLC-UV under LC-MS condition

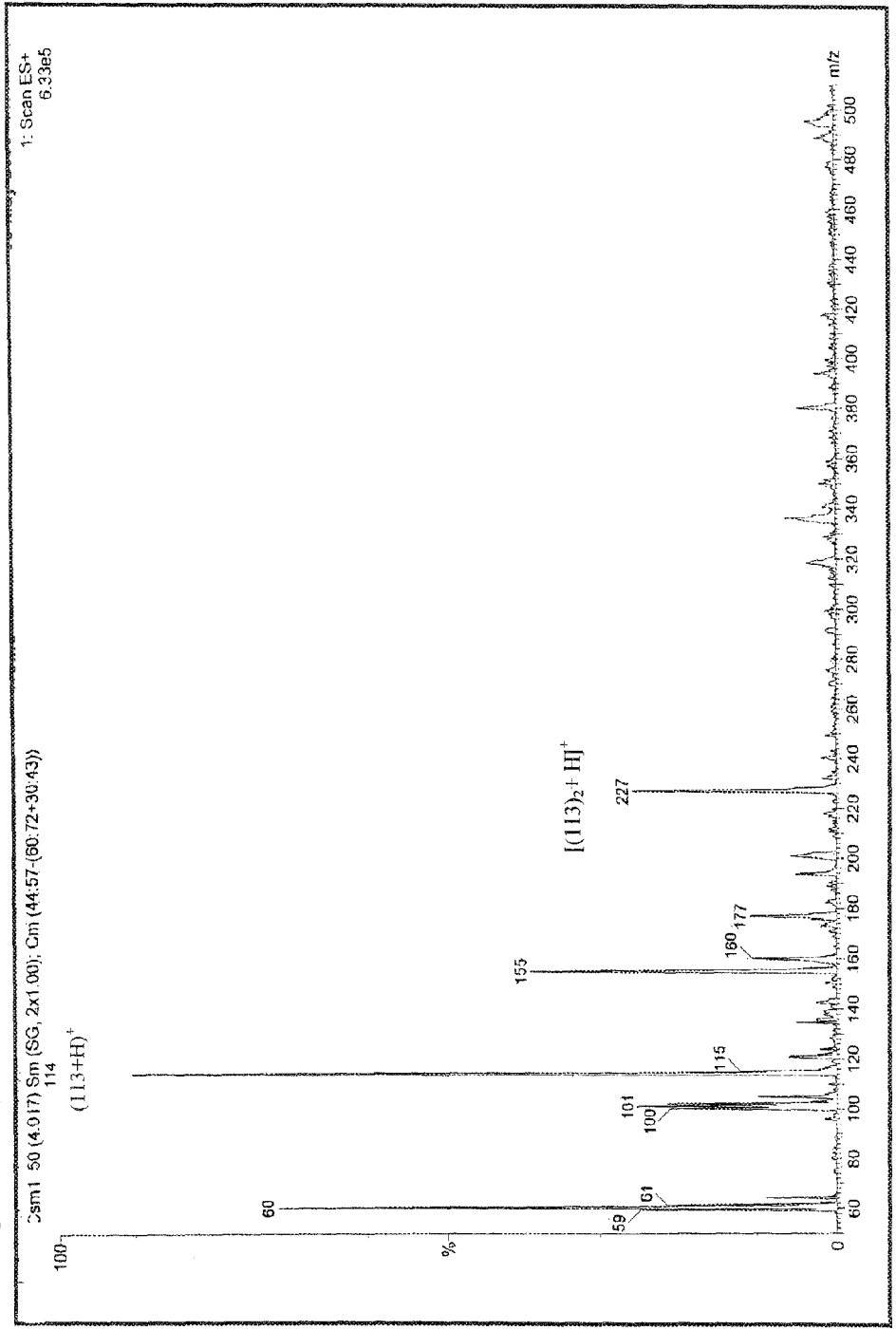
Figure: 11-a of Example 15
Mass Spectrum of peak identified at 4.0 min. (as Figure: 10) during LC-MS run

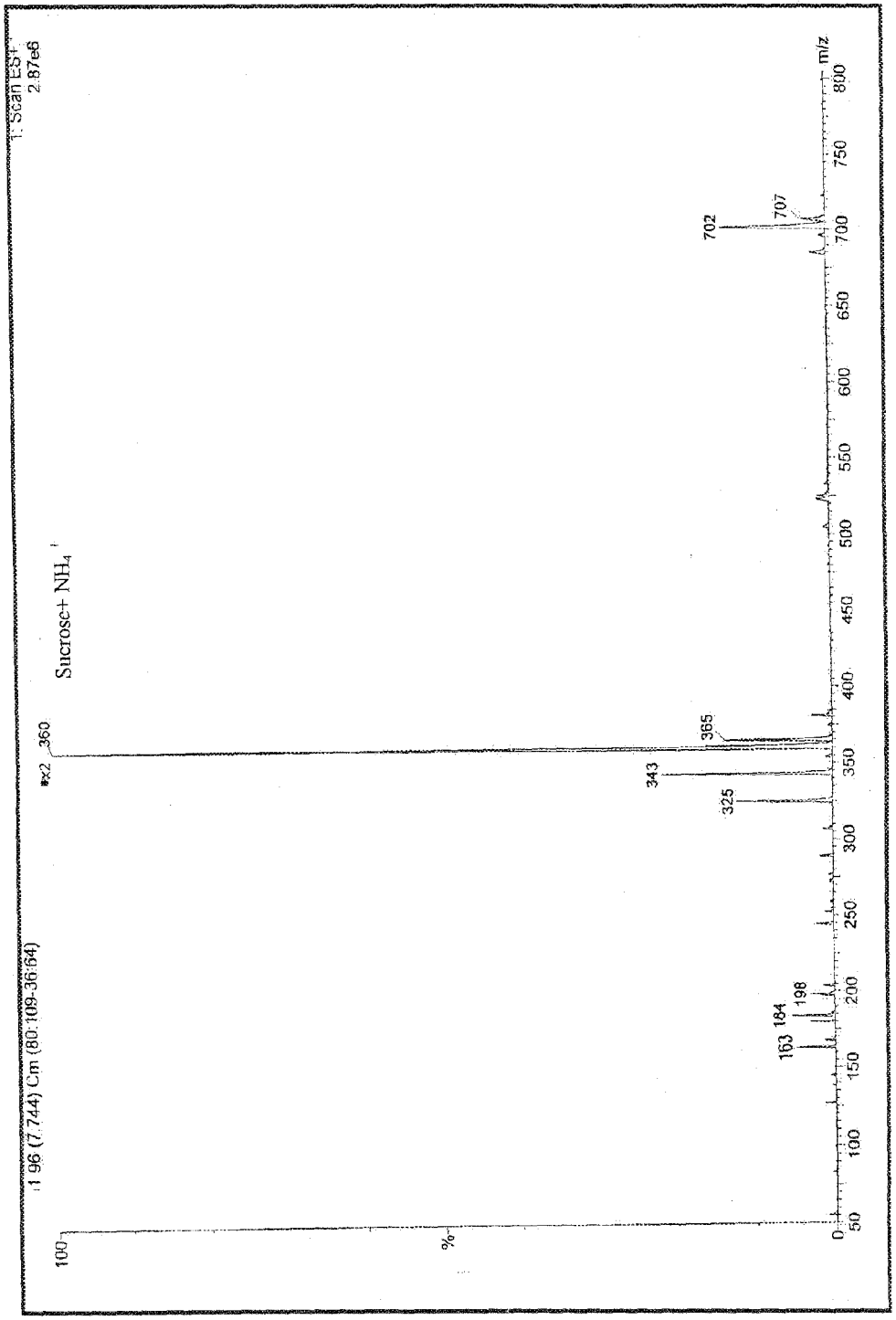
Figure: 11-b of Example 15
Mass Spectrum of Sucrose peak not detected under UV at 7.0 min (as Figure: 10) during LC-MS run

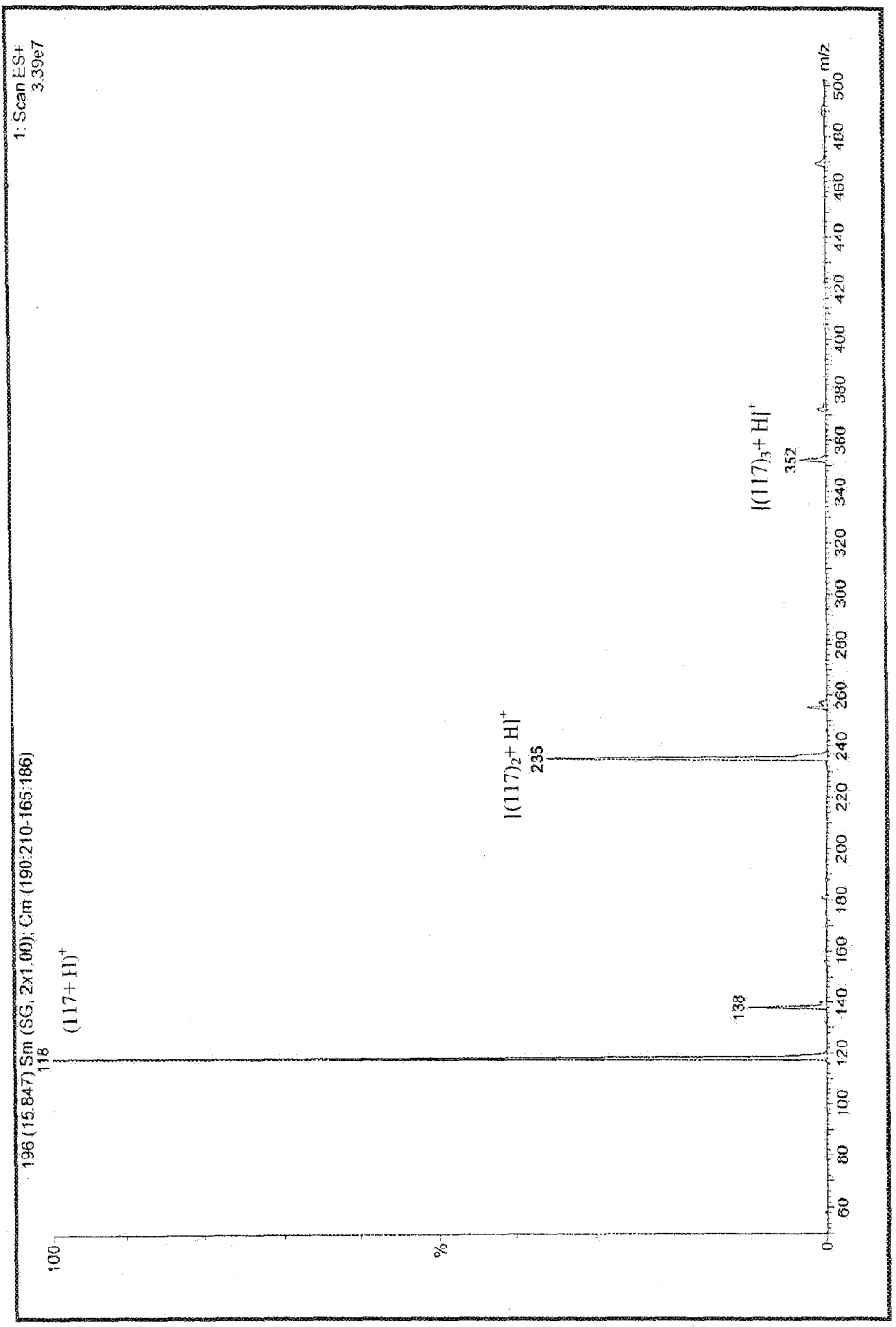
Figure: 11-c of Example 15
Mass Spectrum of peak identified at 15.92 min. (as Figure: 10) during LC-MS run

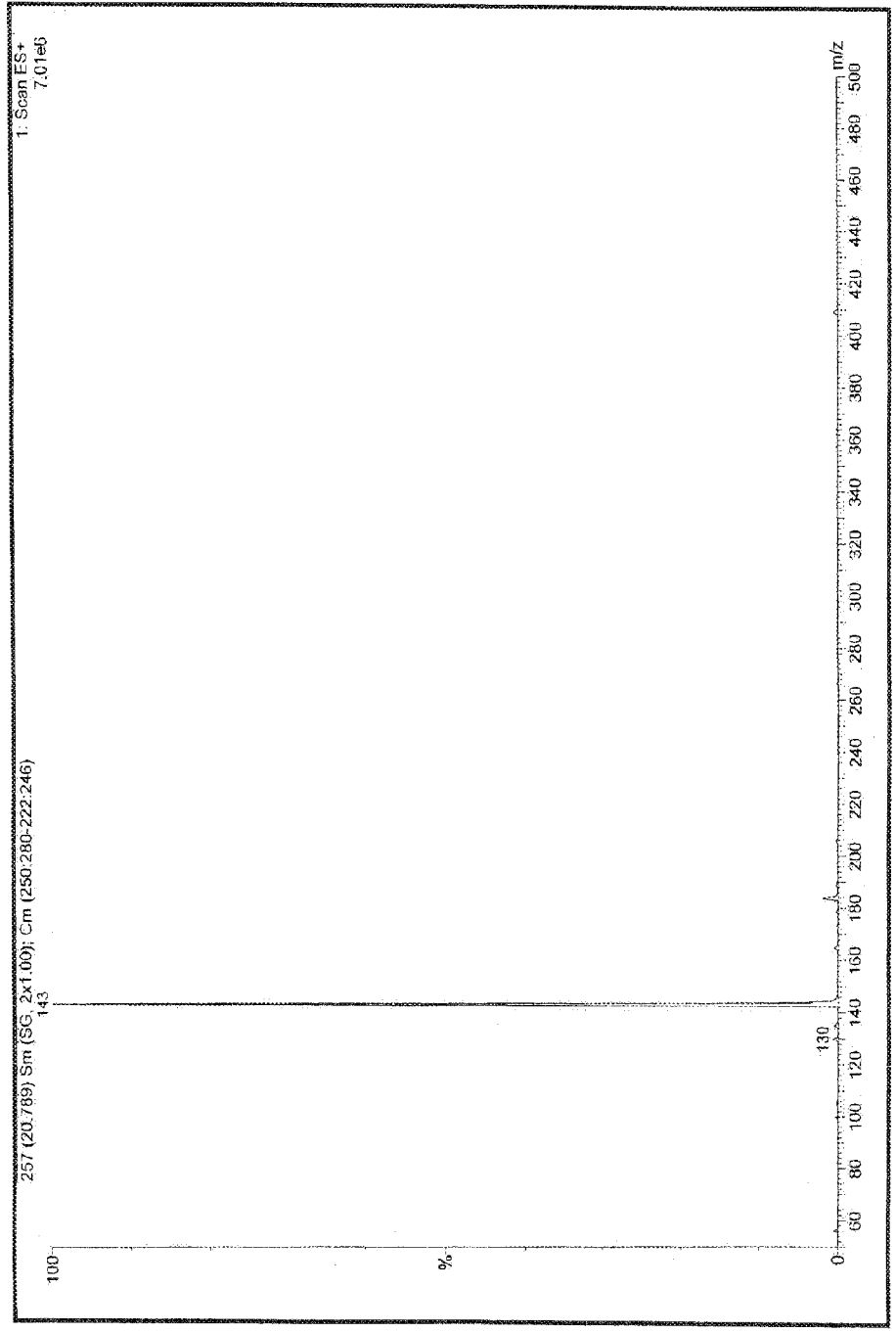
Figure: 11-d of Example 15
Mass Spectrum of peak identified at 20.74 min. (as Figure: 10) during LC-MS run

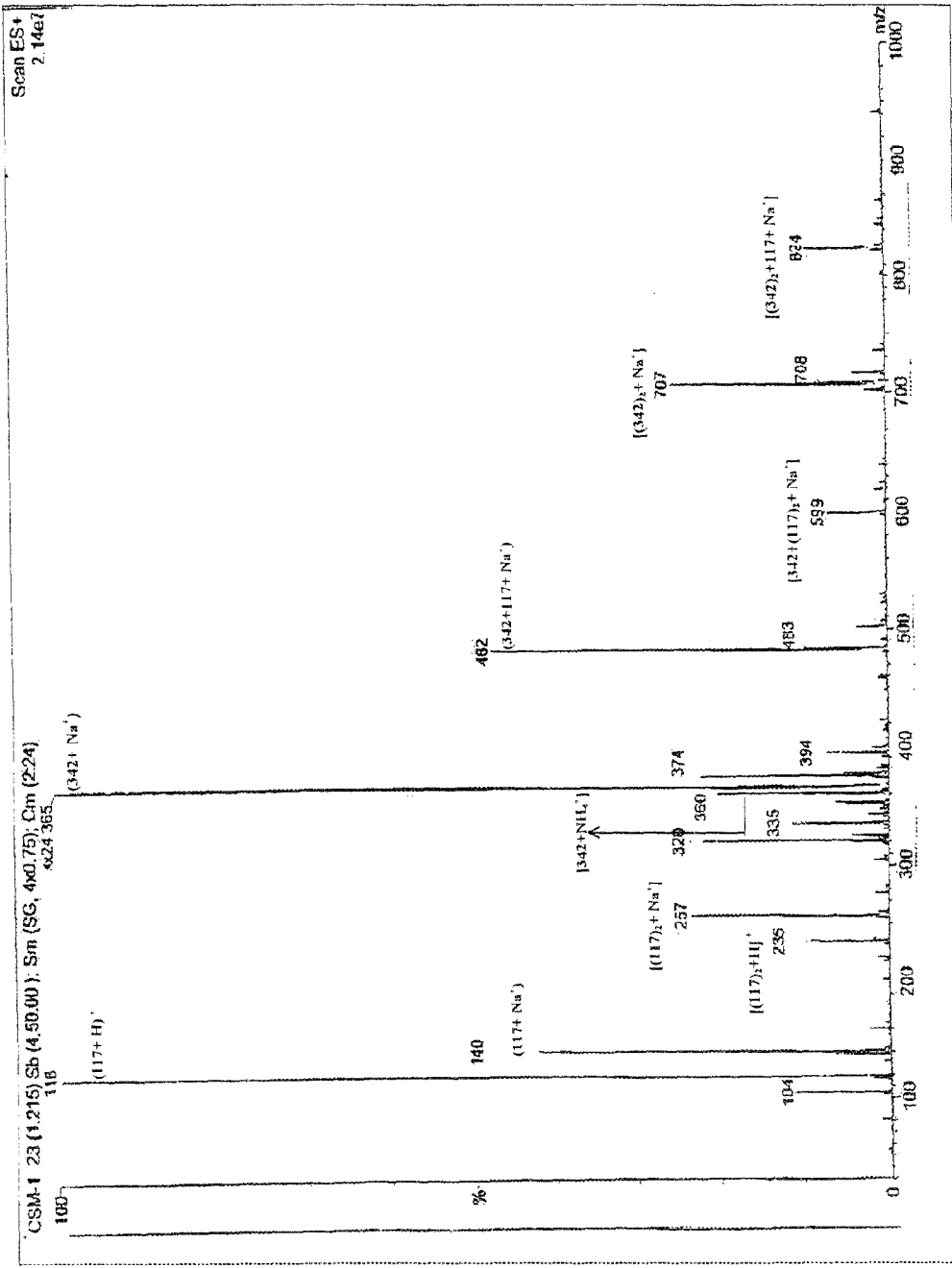
Figure: 12 of Example 15
Mass Spectrum ES+ Scan of SF3-K

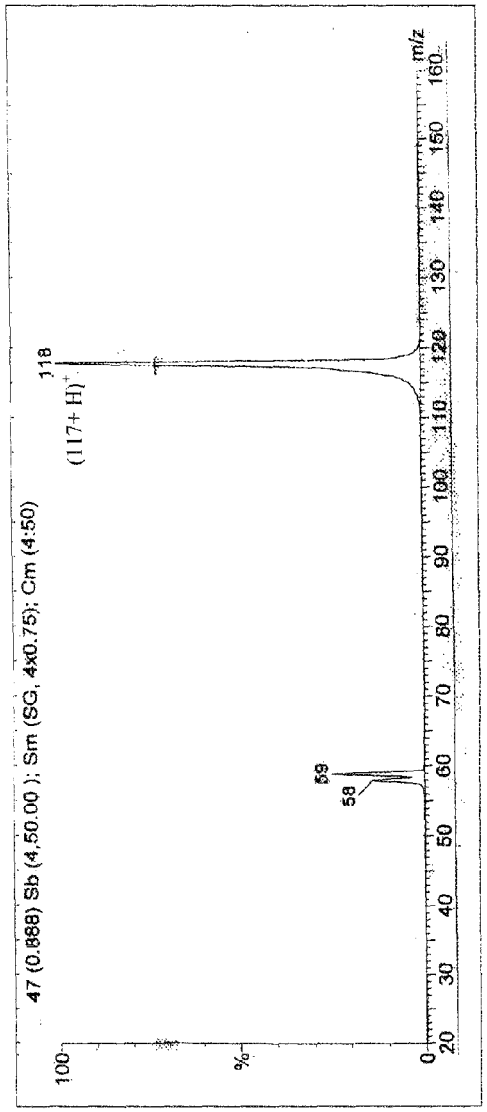
Figure: 13-a of Example 15
MS/MS indicating daughter peaks of m/z=118
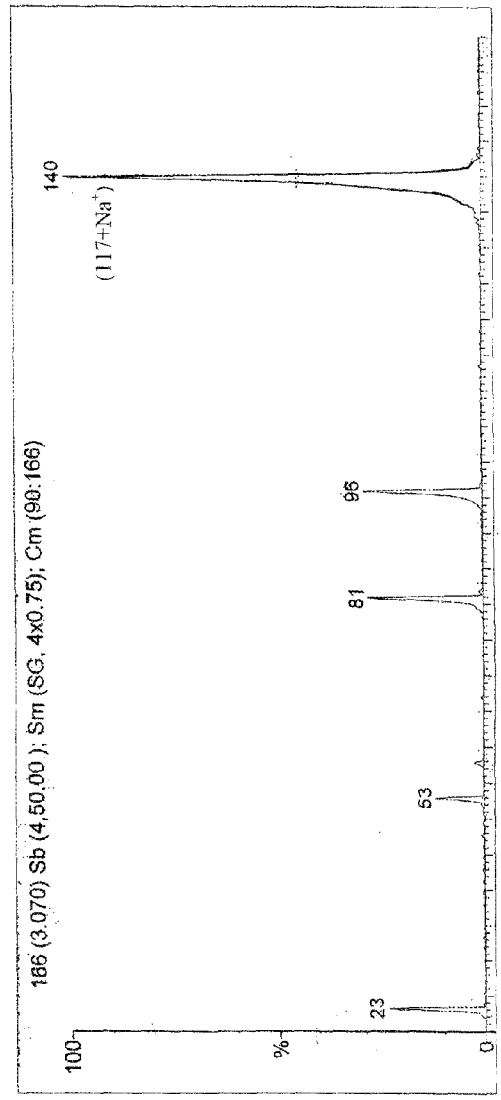
Figure: 13-b of Example 15
MS/MS indicating daughter peaks of m/z=140

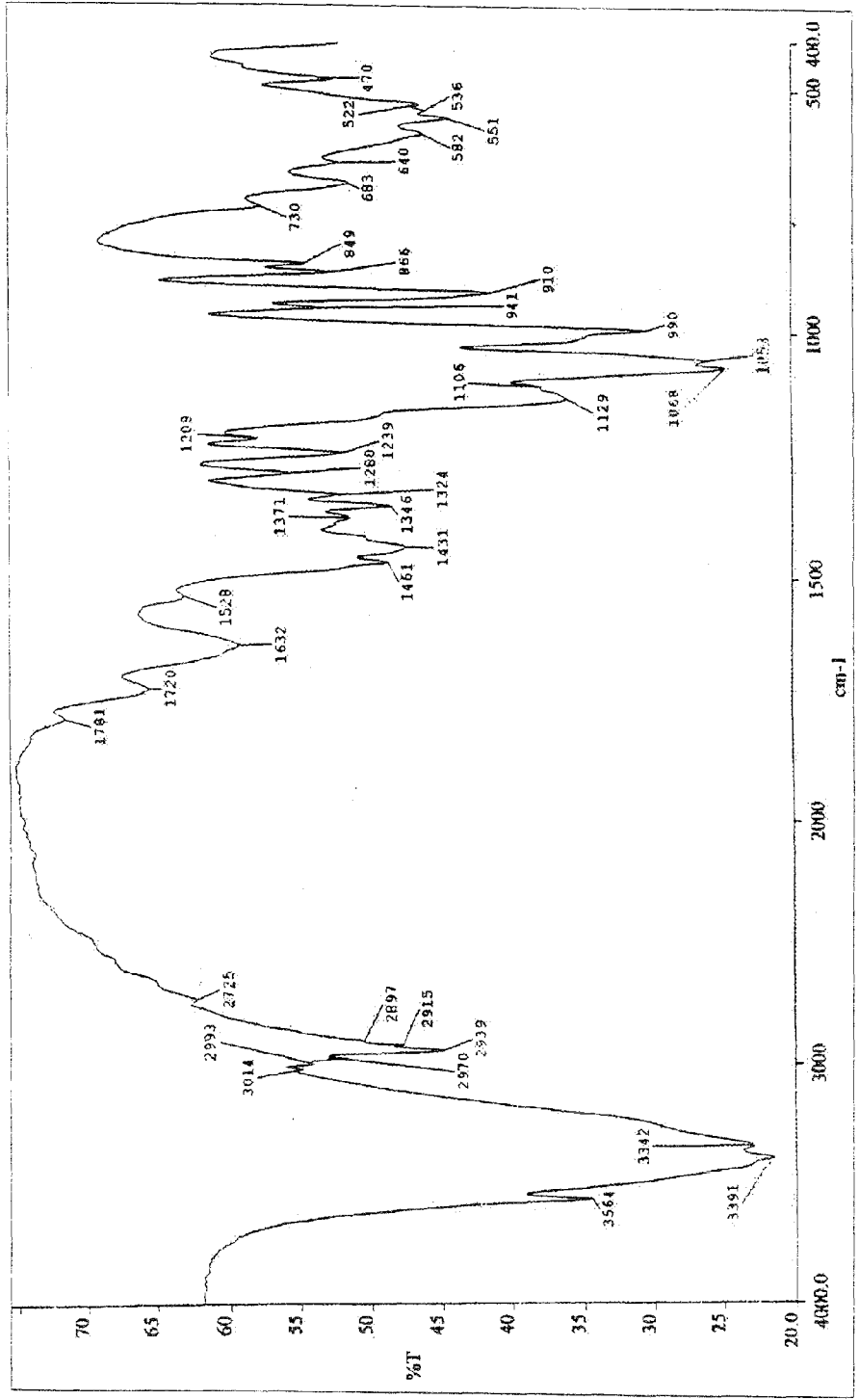
Figure-14-a of Example 15
FT-IR Spectra of SF3-K on KBr Pellet

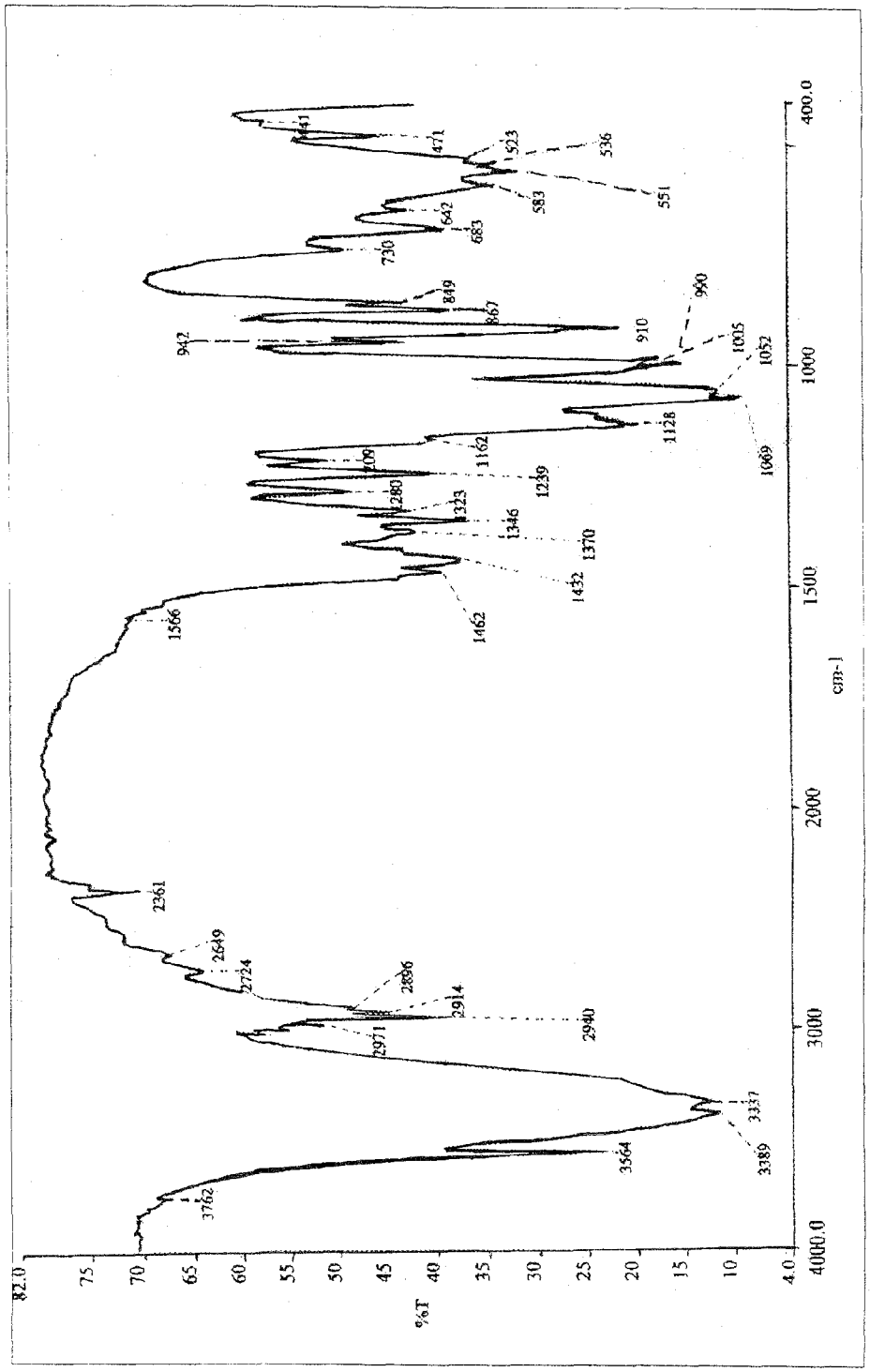
Figure-14-b of Example 15
FT-IR Spectra of Standard Sucrose (Sigma) on KBr Pellet

ANTITUBERCULAR EXTRACTS OF SALICORNIA BRACHIATA

This application is a continuation application of U.S. Ser. No. 11/138,674 filed May 27, 2005 now abandoned. This application claims benefit of IN 0969/DEL/2004, filed 28 May 2004, the entire contents of each of which are hereby incorporated by reference.

FIELD OF THE INVENTION

The present invention relates to an anti-tubercular extract of *Salicornia* species. More particularly, the invention relates to enhancement of anti-tubercular activity of the 1:1 chloroform-methanol fraction of root extract of *Salicornia brachiata* growing naturally along the Gujarat coast of India.

BACKGROUND OF THE INVENTION

Antitubercular chemotherapeutic drugs presently used all over the world comprise primarily of synthetic drugs, e.g., Isoniazid (i.e. Isonicotinic acid hydrazide) used singly or in combination with sodium PAS (Sodium para amino salicylate), Isonex, Erbazide (Calcium methane sulfonate of Isoniazid), Cyclocerine, Morphazinamide hydrochloride, Rifampicin, Ethambutol/Myambutol, Sparfloxicin etc. which were developed subsequent to the synthesis of the antibiotic *Streptomycin*.

While there are cures for tuberculosis by using the above-mentioned drugs along with the BCG vaccination, several drawbacks are noticed, especially in terms of side effects of such drugs, the requirement of prolonged intake/duration of therapy. Another problem observed is that even after treatment, some mycobacterium continues to reside in the subject. It is therefore imperative to create alternatives to the above class of drugs so that either the dosage or the intake duration is reduced or the problem of resistance to the drugs is obviated.

Reference is made to Raritan, N.J. in a science article entitled "Novel Antibiotic shows promise in shortening treatment duration of Tuberculosis" published in BioSpace by AstraZeneca press (2005), describing a compound which belongs to a new family of anti TB agents called diarylquinolines (DARQ) as a better and promising drug individually and in combination than triple cocktail regimen currently recommended by World Health Organization A cocktail regimen containing DARQ cleared infection in mice in half the time than the currently used regimen. It further also stated that no new anti-TB drugs have been brought into the clinic in the past 40 years and although doctors have effective first-line TB drugs that work, there have been difficulties getting these medicines to the patients who need them as well as effectively treating patients with drug resistant diseases. However, this drug is tested on mice and considerable work needs to be done to fully determine this compound's clinical potential.

Similar such reference is also made to an issue dedicated to TB in Journal of Indian Medical Association, vol 101. No. 03 (March 2003), Edited by Subhas, Ch. Chakrabortti under TB Control—The Government & The Private Sector Alliance in which great significance is attached to alternative therapy of existing TB drug therapy & research in alternative MDR therapy under Govt. of India policy of RNTCP. It also highlights that nearly 50000 deaths are taking place in India with 2 million new cases registered every year.

Reference is also made to Jan Koci et. al., in a paper entitled "Heterocyclic Benzazole Derivatives with Antimycobacterial In Vitro Activity" in Bioorganic & Medicinal Chemistry Letters 12 (2002) 3275:278, describes the series of 2-benzylsulfanyl derivatives of benzoxazole and benzothiazole synthesized, and evaluated for their in vitro antimycobacterial activity against *Mycobacterium tuberculosis* and non-tuberculous mycobacteria, and the activity expressed as the minimum inhibitory concentration (MIC) in mmol/L. The substances bearing two nitro groups (4e, 4f, 5e, 5f) or a thioamide group (4i, 4j, 5i, 5j) exhibiting appreciable activity particularly against non-tuberculous strains. However, the most active compounds were subjected to the toxicity assay and were evaluated as moderately cytotoxic.

Reference may also be made to Sandra M. Newton et. al., in a paper entitled "The evaluation of forty-three plant species for in vitro antimycobacterial activities, isolation of active constituents from *Psoralea corylifolia* and *Sanguinaria canadensis*" in the Journal of Ethnopharmacology 79, 57-67 (2002), describes the extracts from forty-three plant species were selected on account of reported traditional uses for the treatment of TB and/or leprosy. These were assayed for anti-mycobacterial activities A simple in vitro screening assay was employed using two model species of mycobacteria, *M., aurum* and *M. smegmatis*. Crude methanolic extracts from three of the plants, *C. mukul, P. corylifolia* and *S. canadensis*, were found to have significant antimycobacterial activity against *M. aurum* only (MIC=62.5 µg/ml). Bioassay guided fractionation led to the isolation of two known benzophenanthridine alkaloids, sanguinarine (1) and chelerythrine (2), from the roots *S. canadensis* and the known phenolic merotepene, bakuchiol (3) from the seeds of *P. corylifolia*. The fractionation of the resin of *C. mukul* lead to a decrease in antimycobacterial activity and hence further work was not pursued. Compound (2) was the most active against *M. aurum* and *M. smegmatis* (IC50=7 30 µg/ml [19.02 µM] and 29 0 µg/ml [75.56 µM], respectively). *M. aurum* was the most susceptible organism to all three compounds. No significant difference in antimycobacterial activity was observed when the two alkaloids were tested for activity in media of differing pH values. The activities of the pure compounds against *M. aurum* were comparable with those against M. bo_is BCG with compound (2) being the most active (M. bo_is BCG, IC50=14.3 µg/mL [37.3 µM]). These results support the use of these plants in traditional medicine. The drawback of the present invention is the in-vivo study is not conducted for further confirmation of activity.

Reference is also made to Usha K. et al., who in a paper entitled "Antitubercular potential of selected plant materials" in Journal of Medicinal and Aromatic plant Sciences, 22/4A-23/1A, 182-184 (Eng.)(2001), describe the anti-tubercular potential of the plants viz., neem, tulsi, garlic, ginger and adhatoda, which were tested by in-vitro culture using 100 mL of aqueous puree (50% w/v) of plant material added to sputum and then inoculated in to L. J medium. All the plant extracts arrested the growth of *Mycobacterium tuberculosis*, which was ascribed to enzymic and nonenzymic antioxidants such as Catalase, peroxidase, total carotene, ascorbic acid, tocopherol, and polyphenols thus preventing tissue damage by ROS (reactive oxygen species). Besides the large quantity of potion that needs to be applied, it is unclear as to the extent of inhibition and the MIC of the potion.

Reference is made to N. Lall et al in a paper entitled "In vitro inhibition of drug-resistant and drug-sensitive strains of *Mycobacterium tuberculosis* by ethno-botanically selected South African plants" in Journal of Ethno pharmacology, 66, 347-354 (1999), which describes the preliminary screening of 20 South African medicinal plant extracts against a drug-sensitive strain, H37Rv, of *Mycobacterium tuberculosis* by agar plate method (Middlebrook and Cohn, 1958). Herein the author ascribes 14 out of 20 acetone extracts showing inhibitory activity at concentration of 500 µg/mL whereas acetone as well water extracts of plant species namely *Cryptocarya latifolia, Euclea natalensis, Helichrysum melanacme, Nidorella anomala* and *Thymus vulgaris* indicated MIC of 100 µg/mL against H37Rv strain by radiometric method.

Reference is also made to Cantrell, Charles L. et al. in a review article entitled "Antimycobacterial plant terpenoids" in Journal of Planta Medica, 67(8), 685-694. (Eng.) (2001), which covers recent report on plant-derived terpenoids that have demonstrated moderate to high activity in In-vitro bioassays against *M. tuberculosis*. In this review, mono-, sesqui-, di- and triterpenes and sterols, their structural analogue and semi synthetic derivatives have been discussed with particular emphasis on the structural features essential for Antimycobacterial activity.

Reference is made to Ma, Junrui in a patent entitled "Compositions containing herbal medicine for pulmonary tuberculosis" No. CN 1265315 A 6 Sep. 2000, 4 pp. (Chinese) (2001), which contains the different forms of composition (aerosol, inhalant, tablet, capsule, powder, oral concentrate and liquid) for treating pulmonary tuberculosis composed of *Taraktogenos, Coptis, Stemona, Cordyceps, Scutellaria, Lonicera japonica, Forsythia vahl, Herba violae, Anemarrhena, Salvia miltiorrhiza, Fructus mume, Ginkgo biloba, Anacamptis pyoamidalis Richard, Polygonatum, Glycyrrhiza, Polygonum multiflorum thunb, Brunella vulgaris, Cirsium japonicum*, leaf of *Thuja ortentalis, Sguisorba officinalis, Heracleum*, common *Andrographis, Houttuynia, herba artemistae* and *Magnolia officinalis*. However the drawback here is the use of multiple herbs for the purpose of elucidating the positive gains of plant against *mycobacterium tuberculosis* and without referring to MIC level either of individual herb or collectively of the combination.

Reference is made to a paper titled "Preliminary antimicrobial screening four South African *Asteraceae* species" by F. Salie, P F K Eagles and H M J Leng in Journal of Ethanopharmacology 52(1996), 27-33 pp., wherein the author has investigated the flora of the Western Cape—a part of Cape Floral kingdom in South Africa. The author ascribes efficacy of four *Asteraceae* species (*Arctopis auriculanta, Ertocephalus africanus* L. *Felicia erigeroides* DC. and *Helichrysum crispum* (L.) D. Don.) exhibiting selective antimicrobial activity to various degrees for *Mycobacterium smegmatis*. Identifying the 8500 µg/mL. of MIC in leaves of *Arctopis auriculanta*. The drawback of the invention is the very high MIC value.

Reference is also made to the Internet website benefits@coqui.net on *Salicornia* plant wherein the use of the *Salicornia* plant as a source of edible oil and use of dried crushed stems as fuel briquettes or particleboard are reported. However, there is no mention of any bioactivity of the plant.

Reference is also made to U.S. patent application Ser. No. 10/106,334 dt. 26$^{th}$ Mar. 2002 by P. K. Ghosh et. al. wherein a vegetable salt preparation from residual dry matter after removal of seeds using the halophyte has been described to maximize the value derived from the plant. However this application does not provide any utilization of the plant for drug/medicinal purpose.

Reference is made to Wealth of India, vol. IX RH-SO, Raw Material Page No. 169 which documents various bioresources of India and application thereof has listed *Salicornia* Linn and its taxonomy beside use of the species as fodder. The plant is also listed in Flora of India by Hooker (1889), However no mention is made in both documents on any kind of bioactivity associated with *Salicornia*. It is a small genus of annual or perennial leafless fleshy herbs or shrubs, native to salt marshes of Asia, Africa, Europe and North America. Only one species occurs in India. D.E.P. VI (2), 387:1, 399:II, 60, Fl. Br. Ind., V.12 Kirt. and Basu, Pl. 800. It is known under different name in various regions of India as: Gujarati.— Muchul, Telugu:—Kagalu, Tamil & Malayalam: Umari Keerai.

It is a perennial much branched, herbaceous plant with jointed stamps 30-45 cm. High found in salt marsh along with the sea coast from Bengal to Gujarat. Branches rather slander joints 6-12 mm. long; flowers sunk in cavities of the joints, three on each side, fruits membranous.

The plant is a source of alkaline, earth or *saji* used for extracting sodium carbonate The ash of the plant called *saji* or *barilla* was formerly used in soap and glass making. Air dried plant contains 6.98% protein (N×6.25) and 8.97% ash. It contains of high percentage of sodium chloride ions which constitutes C 86% of total water soluble salt. Water extractable mineral are Cl=10.02 m, Na=5.6, S=0.70, P=1.13, C=0.72, Ca=0.01, Mg=0.02%. (Parekh and Rao. curr. Sci. 1965, 34; 247). The plants are strongly salty nature, lower and young shoots are eaten after pickling. The shoots are sometimes used at pot-herb. The plants are used as camel fodder also (Mc Canr, J. Bombay Nat. Hist. Soc, 1951-52, 50, 870) The ashes are used in mange and itch, and are also considered to be emmengogue and abortifacient (Kirt. and Basu, III 2082).

Reference is made to U.S. patent application Ser. No. 10/829,400 dated 22$^{nd}$ Apr. 2004 and PCT patent application No. PCT/IN03/00292 dated 29$^{th}$ Aug. 2003 by Rathod et al. where activity of *Salicornia brachiata* growing naturally in the Gujarat coast of India against *M. Tuberculosis* is disclosed. The main drawback of the application is that the HPLC of the fraction is too complex and provides little clue of the nature of the constituents in the active fraction. Moreover, the maximum inhibition in in-vitro studies was only 75% when the dosage was 6.25 µg/mL.

OBJECTS OF THE INVENTION

The main object of the invention is to provide the bioactive fractions from *Salicornia* species.

Another object of the present invention is to identify the source of anti TB activity in the F2 fraction of the root extract of *Salicornia brachiata* as previously disclosed by the applicants in their pending U.S. patent application Ser. No. 10/829, 400 dated 22$^{nd}$ Apr. 2004 and PCT patent application No. PCT/IN03/00292 dated 29$^{th}$ Aug. 2003.

Further object is to improve the chromatographic separation condition to resolve the various peaks in the active fraction as reported in the prior art for separation through semi-preparative HPLC.

Another object is to correlate the different sub-fractions obtained from the active fraction with their activities.

Another object is to demonstrate the efficacy of the most active sub-fraction against tuberculosis both in vitro and in vivo against infected mice.

Another object is to show that the MIC of the most active sub-fraction is ≦3 125 µg/mL.

Another object is to show enhanced survival duration of infected mice that have been administered the active sub-fraction orally at a dosage of 50 mg/kg body weight.

Another object is to show that the most active sub-fraction has no observable toxicity through cytotoxicity studies using VERO cell line.

Another object is to show that healthy mice which have been administered the active fraction remain healthy and gain weight thereby demonstrating the non-toxic nature of the active sub-fraction.

Another object is to characterize the constituents of the active sub-fraction.

Another object is to show that sucrose is the principle component of the sub-fraction and further that there are minor constituents that co-elute with the sucrose.

Another object is to demonstrate that sucrose alone has no anti-TB activity and that activity lies in the minor constituents that act singly or in combination with other minor constituents and/or the major constituent.

Another object is to utilize the most active sub-fraction as a possible cure for tuberculosis either as is or through further purification to enhance activity still further.

Another object is to separate and individually study the minor constituents for their anti-TB activity.

SUMMARY OF THE INVENTION

Accordingly, the present invention provides bioactive fractions from extracts of *Salicornia* species.

The invention also provides a means of enhancing the anti-tubercular activity of the chloroform-methanol (1:1) fraction obtained from the roots of matured *Salicornia brachiata* as disclosed in the pending U.S. patent application Ser. No. 10/829,400 dated 22$^{nd}$ Apr. 2004 and PCT patent application No. PCT/IN03/00292 dated 29$^{th}$ Aug. 2003.

In one embodiment of the invention, the *Salicornia* species comprises of *Salicornia brachiata*, preferably a mature plant, and wherein the preferred plant parts extracted are selected from the group consisting of whole plant without root, roots, spikes, husk and seeds.

In another embodiment of the invention, the bioactive fractions comprise F1, F2, F3, F4 and F5.

In another embodiment of the invention, the bioactive fraction F2 further comprising sub-fractions SF1, SF2, SF3, SF4, SF5, SF6 and SF7.

In another embodiment of the invention, the SF3-K is the sub-fraction of SF3.

In another embodiment of the invention, the SF3-K is stable for 4 hours even at a temperature ranging upto 50° C.

In another embodiment of the invention, the major constituent of SF3K comprising Sucrose to the extent of 75-80% based on HPLC with RI detection.

In another embodiment of the invention, the bioactive fraction possess antitubercular activity and is useful as an antitubercular agent.

In one embodiment of the invention, the MIC value of the anti-tubercular fraction (henceforth referred to as SF3-K) of this invention is ≦3.125 µg/mL when tested against *M. tuberculosis* H37Rv on 7H10 Middlebrook's medium containing OADC.

In another embodiment SF3-K shows complete inhibition against *M. Tuberculosis* H37Rv at dosage of 50 µg/mL and 100 µg/mL when evaluated in vitro by the BACTEC method and further shows dose dependence of the growth index.

In another embodiment SF3-K exhibits no cytotoxicity in tests conducted with the VERO cell line even for dosage up to 100 µg/mL, i.e., beyond ten times the MIC value of SF3-K as estimated by the method of claim 1.

In another embodiment SF3-K is also active in vivo and increases the mean survival time (MST) of infected mice by 5 days when a dose of SF3-K amounting to 50 mg/kg of body weight is administered orally for 12 days after infection.

In another embodiment SF3-K shows no toxicity towards healthy mice administered SF3-K orally at the dosage of 50 mg/kg of body weight.

In another embodiment SF3-K is shown to comprise of mainly Sucrose [75-80%] on the basis of HPLC-RI detector], the balance being minor constituents having molecular weights of 113, 115, 117. Another constituent has m/z of 143 [142+H$^+$].

In another embodiment of the invention, anti-tubercular activity of SF3-K is shown to reside in the minor constituents of the fraction that amount to only 20-25% of the weight of the fraction.

Accordingly the present invention provides a process for preparation of bioactive fractions from extracts of *Salicornia* species comprising the following steps:

(i) providing F2 fraction from *Salicornia brachiata* according to the procedure claimed in U.S. patent application Ser. No. 10/829,400 dated 22$^{nd}$ Apr. 2004 and PCT patent application No. PCT/IN03/00292 dated 29$^{th}$ Aug. 2003, the contents of which are incorporated herein by reference, (ii) subjecting the F2 Bioactive fraction to sub-fractionation on Semi-preparative HPLC using RP-18 column (Phenomenex) and 03:97::CH$_3$CN:H$_2$O mobile phase at 7 mL/min, (iii) collecting seven sub-fractions SF1, SF2, SF3, SF4, SF5, SF6 and SF7 between 0 to 22 minutes as per the Semi-prep HPLC profile provided in the application;

(iv) subjecting the sub-fractions obtained in step (iii) to anti-tubercular screening;

(v) identifying the sub-fraction SF3 as best compromise in terms of activity of sub-fraction and quantity of material obtained;

(vi) concentrating the sub-fraction obtained in step (v) and re-chromatographing on the same semi-preparative column (keeping all conditions same except alteration of flow rate to 6 to 7 mL/min) to enhance the purity of the peak having retention time of 11.89 min at 6 mL/min flow rate on Semi-preparative column and retention time of 2.95 min at 1 mL/min flow rate on analytical column;

(vii) concentrating the fraction obtained in step (vi) and subjecting to freeze drying to obtain SF3-K.

In another embodiment of the invention, wherein the fraction obtained in step (vi) subjected to freeze drying to obtain solid SF3-K in the range of 0.6 to 0.9% yield from dry root.

In another embodiment of the invention, the reverse phase chromatographic separation of the chloroform-methanol fraction is improved over that reported in the pending patent application by altering the mobile phase to acetonitrile: water: 03:97 that enabled sub-fractionation of the fraction into seven distinct parts (sub-fractions) and identification of one sub-fraction (SF3) as most desired from the joint consideration of anti-tubercular activity and quantity of material obtained.

In another embodiment SF3 was re-chromatographed and further purified to obtain SF3-K as an apparently single peak on the analytical reverse phase column.

In still another embodiment of the present invention, SF3-K was concentrated on a rotary evaporator in a temperature range of 45 to 55° C.

In still another embodiment of the present invention, the concentrated extract may be freeze dried in the temperature range of −50 to −60° C. for a period of 8 to 16 hours.

In still another embodiment of the present invention, SF3-K was exposed for 4 hrs. to the hot afternoon sun and found to be stable.

In another embodiment of the present invention, the SF3-K was chromatographed on a Waters Amino column and eluted with 80:20::$CH_3CN:H_2O$ whereupon the various constituents of SF3-K could be resolved and their molecular weights based on Mass Spectroscopy were determined to be 113, 342 (Sucrose), 115 and 117. A minor constituent having m/z of 143 was also observed at long retention time.

In an embodiment of the invention wherein for characterization of the constituents of SF3-K the constituents of SF3-K were resolved by subjecting it to liquid chromatography on Waters Amino column using 80:20::$CH_3CN:H_2O$ and monitoring minor and major constituents both with UV (210 nm) and RI detectors and analyzing for the constituents using LC-MS.

The bioactive fractions obtained from an extract of *Salicornia* species useful as an antitubercular agent.

In an embodiment of the invention, wherein the *Salicornia* species comprises of *Salicornia brachiata*.

In an embodiment of the invention, wherein the *Salicornia brachiata* is a fully matured plant.

In another embodiment of the invention, wherein the bioactive extract comprises extracts from parts of *Salicornia* plant selected from the group consisting of whole plant without root, roots, spikes, husk and seeds.

In still another embodiment of the invention, wherein the bioactive fractions comprise F1, F2, F3, F4 and F5.

In a further embodiment of the invention, wherein the fraction F2 is further comprising sub-fractions into SF1, SF2, SF3, SF4, SF5, SF6 and SF7.

In an embodiment of the invention, wherein the sub-fraction SF3 is further fractionated into SF3K.

In still another embodiment of the invention, wherein the major constituent of SF3K comprising Sucrose to the extent of 75-80% based on HPLC with RJ detection.

In an embodiment of the invention, wherein the said fraction possess antitubercular activity.

In an embodiment of the invention, wherein the fraction SF3K exhibits an MIC value $\leq 3 125$ μg/mL against *M. tuberculosis* H37Rv when evaluated using 7H10 Middlebrook's medium containing OADC (B-D, USA).

In an embodiment of the invention, wherein the fraction SF3K exhibits complete inhibition against *M. Tuberculosis* H37Rv at dosage of 50 μg/mL and 100 μg/mL when evaluated in-vitro by the BACTEC method and further shows dose dependence of the growth index.

In an embodiment of the invention the bioactive fraction is also active in-vivo and increases the mean survival time (MST) of infected mice by 5 days when a dose of SF3-K amounting to 50 mg/kg of body weight is administered orally for 12 days after infection.

In an embodiment of the invention, that fraction exhibits no cytotoxicity in tests conducted with the VERO cell line even for dosage up to 100 μg/mL, i.e., beyond ten times the NHC value of SF3-K.

In an embodiment of the invention. Fraction shows no toxicity towards healthy mice administered SF3-K orally at the dosage of 0 to 50 mg/kg of body weight.

In an embodiment of the invention wherein the major constituent sucrose is unlikely to have any activity as pure sucrose even for dosage of 100 μg/mL.

In an embodiment of the invention, wherein the most prominent minor constituent exhibits m/z values of 118 [117+H]$^+$ and 140 [117+Na$^+$] corresponding to a molecular weight of the constituent of 117.

In an embodiment of the invention, wherein the minor constituent having molecular weight of 117 shows daughter peaks corresponding to m/z values of 58 and 59 whereas in the form of sodium salt daughter fragments are found with m/z values of 96, 81, 53 and 23.

In an embodiment of the invention, wherein the constituent having M.W. 117 form self-clusters under the conditions of mass spectroscopy and also clusters with the major constituent (Sucrose).

In an embodiment of the invention, wherein other minor constituents are observed with molecular weights of 113, 115 and 142.

In an embodiment of the invention, wherein the sub fractions SF1, SF5, SF6 and SF7 were also found having anti-tubercular activity at 100 to 12.5 μg/mL & SF2 and SF4 were found having anti-tubercular activity at 100 to 25 μg./mL.

The present invention also provides a method for the treatment of tuberculosis comprising administering to a subject suffering therefrom, a pharmaceutically effective amount of an antitubercular fraction obtained from *Salicornia* species optionally along with any other antitubercular drug of synthetic or natural origin and a pharmaceutically acceptable additive or carrier.

In an embodiment of the invention, wherein the method comprises administering either bioactive fraction or the crude extract of *Salicornia* species to the subject.

In an embodiment of the invention, wherein the *Salicornia* species comprises of *Salicornia brachiata*.

In one of the embodiment of the invention, wherein the *Salicornia brachiata* is a fully matured plant.

In an embodiment of the invention, wherein the fractions comprise F1, F2, F3, F4 and F5.

In an embodiment of the invention, wherein the fraction F2 is sub-fractionated into SF1, SF2, SF3, SF4, SF5, SF6 and SF7.

In an embodiment of the invention, wherein the sub-fraction SF3 is further fractionated into SF3K.

In an embodiment of the invention, wherein the major constituent of SF3K comprising Sucrose to the extent of 75-80% based on HPLC with RI detection.

In an embodiment of the invention, wherein the said fraction possess antitubercular activity.

In an embodiment of the invention, wherein the fraction SF3K exhibits an MIC value $\leq 3.125$ μg/mL against *M. tuberculosis* H37Rv when evaluated using 7H10 Middlebrook's medium containing OADC (B-D, USA).

In an embodiment of the invention, wherein the fraction SF3K exhibits complete inhibition against *M. Tuberculosis* H37Rv at dosage of 50 μg/mL and 100 μg/mL when evaluated in-vitro by the BACTEC method and further shows dose dependence of the growth index.

In an embodiment of the invention, wherein the fraction is also active in-vivo and increases the mean survival time (MST) of infected mice by 5 days when a dose of SF3-K amounting to 50 mg/kg of body weight is administered orally for 12 days after infection wherein the fraction exhibits no cytotoxicity in tests conducted with the VERO cell line even for dosage up to 0-100 μg/mL, i.e., beyond ten times the MIC value of SF3-K.

In an embodiment of the invention, wherein the fraction does not show toxicity towards healthy mice administered SF3-K orally at dosage of 0-50 mg/kg of body weight.

In an embodiment of the invention, wherein the major constituent sucrose is unlikely to have any activity as pure sucrose even for dosage of 100 μg/mL.

In an embodiment of the invention, wherein the most prominent minor constituent exhibits m/z values of 118 [117+H]$^+$ and 140 [117+Na$^+$] corresponding to a molecular weight of the constituent of 117.

In an embodiment of the invention, wherein the minor constituent having molecular weight of 117 shows daughter peaks corresponding to m/z values of 58 and 59 whereas in the form of sodium salt daughter fragments are found with m/z values of 96, 81, 53 and 23.

In an embodiment of the invention, wherein the constituent having M.W. 117 form self-clusters under the conditions of mass spectroscopy and also clusters with the major constituent (Sucrose).

In an embodiment of the invention, wherein other minor constituents are observed with molecular weights of 113, 115 and 142.

In an embodiment of the invention, wherein the fraction is administered in a form selected from tablets, lozenges, capsules, powder, solution, intravenously and orally.

The present invention also provides a pharmaceutical composition comprising bioactive fraction[s] isolated from extracts of *Salicornia* species optionally along with any other anti-tubercular drug of synthetic or natural origin and a pharmaceutically acceptable additive or carrier.

In an embodiment of the invention, wherein the *Salicornia* species comprises of *Salicornia brachiata*.

In an embodiment of the invention, wherein the *Salicornia brachiata* is a fully matured plant.

In an embodiment of the invention, wherein the extract comprises extracts from *Salicornia* plant part selected from the group consisting of whole plant without root, roots, spikes, husk and seeds.

In an embodiment of the invention, wherein the fractions comprise F1, F2, F3, F4 and F5.

In an embodiment of the invention, wherein the fraction F2 further comprising sub-fractions into SF1, SF2, SF3, SF4, SF5, SF6 and SF7

In an embodiment of the invention, wherein the sub-fraction SF3 is further fractionated into SF3K.

In an embodiment of the invention, wherein the major constituent of SF3K comprising Sucrose to the extent of 75-80% based on HPLC with RI detection.

In an embodiment of the invention, wherein the said fraction possess antitubercular activity.

In an embodiment of the invention, wherein the fraction SF3K exhibits an MIC value $\leq 3.125$ µg/mL against *M. tuberculosis* H37Rv when evaluated using 7H10 Middlebrook's medium containing OADC (B-D, USA).

In an embodiment of the invention, wherein the fraction SF3K exhibits complete inhibition against *M. Tuberculosis* H37Rv at dosage of 50 µg/mL and 100 µg/mL when evaluated in-vitro by the BACTEC method and further shows dose dependence of the growth index.

In an embodiment of the invention, that is also active in-vivo and increases the mean survival time (MST) of infected mice by 5 days when a dose of SF3-K amounting to 50 mg/kg of body weight is administered orally for 12 days after infection.

In an embodiment of the invention, that exhibits no cytotoxicity in tests conducted with the VERO cell line even for dosage up to 100 µg/mL, i.e., beyond ten times the MIC value of SF3-K.

In an embodiment of the invention, that shows no toxicity towards healthy mice administered SF3-K orally at the dosage of 0 to 50 mg/kg of body weight.

In an embodiment of the invention, wherein the major constituent sucrose is unlikely to have any activity as pure sucrose even for dosage of 50 to 100 µg/mL.

In an embodiment of the invention, wherein the most prominent minor constituent exhibits m/z values of 118 [117+H]$^+$ and 140 [117+Na$^+$] corresponding to a molecular weight of the constituent of 117.

In an embodiment of the invention, wherein the minor constituent having molecular weight of 117 shows daughter peaks corresponding to m/z values of 58 and 59 whereas in the form of sodium salt daughter fragments are found with m/z values of 96, 81, 53 and 23.

In an embodiment of the invention, wherein the constituent having M.W. 117 form self-clusters under the conditions of mass spectroscopy and also clusters with the major constituent (Sucrose).

In an embodiment of the invention, wherein other minor constituents are observed with molecular weights of 113, 115 and 142.

In an embodiment of the invention, wherein the sub fractions SF1, SF5, SF6 and SF7 were also found having anti-tubercular activity at 100-12.5 µg/mL & SF2 and SF4 were found having anti-tubercular activity at 100-25 µg./mL.

In an embodiment of the invention, wherein the composition is in a form selected from the group consisting of a tablet, lozenge, solution, capsules, powder and solution.

BRIEF DESCRIPTION OF THE ACCOMPANYING DRAWINGS

FIG. 1 is an analytical HPLC profile of the fraction F2 at 254 nm. Using RP-18 column (Phenomenex) and 1:1:: $CH_3CN$:MeOH as isocratic eluting solvent system at a flow rate of 1 mL/min.

FIG. 2 is a analytical HPLC profile of fraction F2 at 220 nm, using RP-18 column (Phenomenex) and 03:97::$CH_3CN$:$H_2O$ as isocratic eluting solvent system at a flow rate of 1 mL/min. that is the starting point of the present invention.

FIG. 4 is a analytical HPLC profile of SF3-K at 220 nm. using RP-18 column (Phenomenex) and 03:97::$CH_3CN$:$H_2O$ as isocratic eluting solvent system at a flow rate of 1 mL/min.

Figure 3:
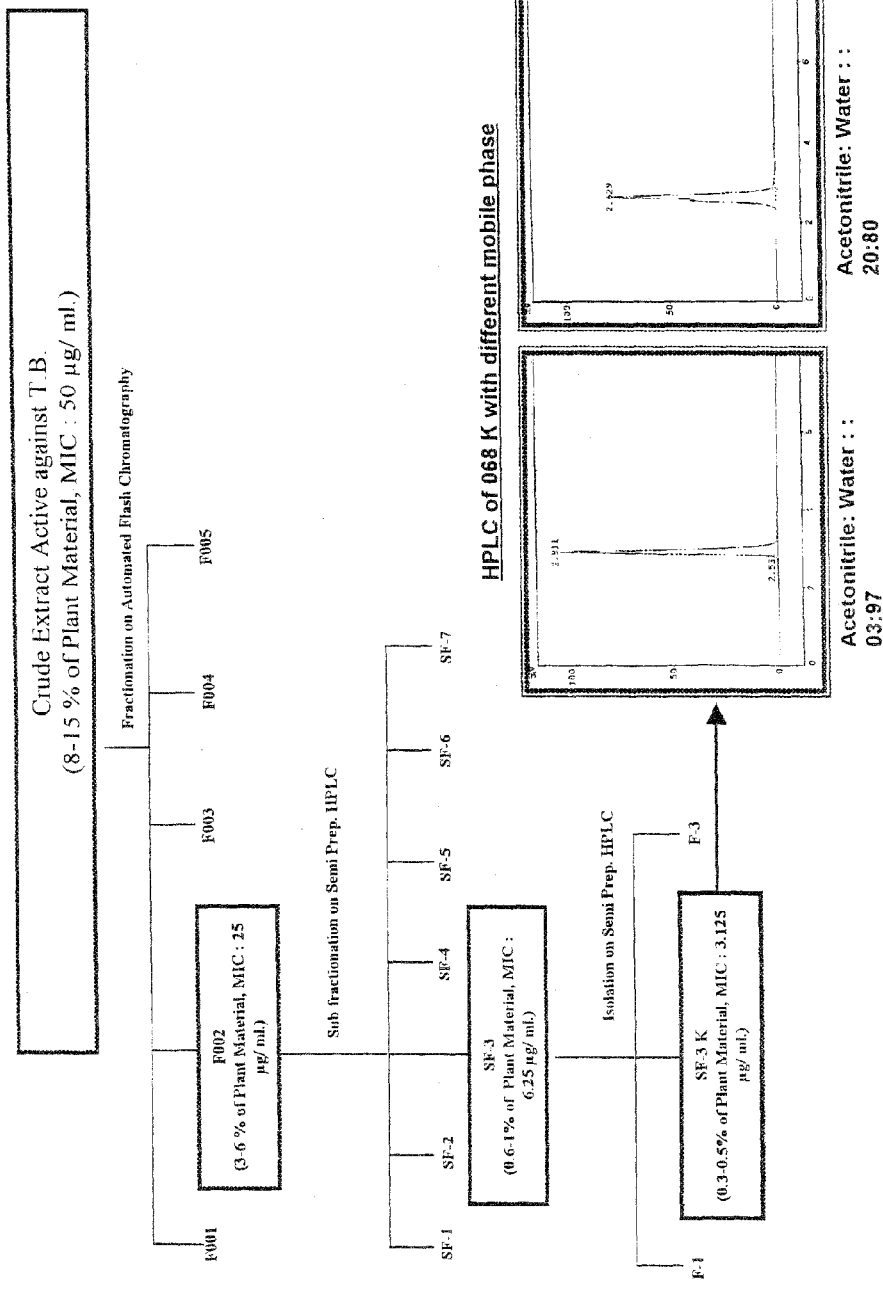
FIG. 3 is a Semi preparative HPLC profile of fraction F2 at 220 nm using RP-18 column (Phenomenex) and 03:97::$CH_3CN$:$H_2O$ as isocratic eluting solvent system at a flow rate of 6 mL./min.

FIG. 5 Protection by SF3-K given orally at the dose of 50-mg/Kg. body weight for 12 days in mice against infection of *M. tuberculosis* H37Rv.

FIG. 6 is a cytotoxic study of SF3-K on VERO cell line method using MTT assay.

FIG. 7 is a TOCSY spectrum (2D) of SF3-K indicating the detachment of minor constituents from major constituent sucrose present in the SF3-K.

FIG. 8 is a Inhibition growth data of *M. tuberculosis* H37Rv by SF3-K with comparison of Sucrose by BACTEC in-vitro screening method for five days.

FIG. 9 is a Repeat experiment data for Inhibition of growth of *M. tuberculosis* H37Rv by SF3-K at two different dose level of 50 and 100 µg./mL conc. in BACTEC.

FIG. 10 is a HPLC-UV profile of SF3-K under LC-MS condition. HPLC was carried out using Waters Amino column with $CH_3CN$:$H_2O$::80:20 as mobile phase.

FIG. 11-*a*, *b*, *c* and *d* are Mass Spectrum of the individual peaks of SF3-K identified in the HPLC-TV run under LC-MS condition as FIG.-10. FIG. 11-*b* is a Mass Spectrum of Sucrose peak, which is not detected under UV at 7.0 min. during LC-MS run of SF3-K.

FIG. 12 is a Mass Spectrum—ES$^+$ Scan of SF3-K.

FIG. 13-*a* & *b* are MS-MS indicating daughters of m/z=118 and m/z=140 respectively.

FIG. 14-a & b are FT-IR spectra of SF3-K and Standard Sucrose on KBr pellet respectively.

DETAILED DESCRIPTION OF THE INVENTION

The present invention relates to the analysis and study of *Salicornia* species in order to obtain bioactive fractions or crude extracts thereof which may possess antitubercular activity. In *Salicornia* genus *Salicornia brachiata* is species native to India and occurs abundantly in coastal mud flats of Western Coast of India and is also reported in the eastern/southern coast. The other species of *Salicornia* are *Salicornia bigelovi*, *Salicornia depressa* and *Salicornia maritima* (Occurring in North eastern U.S.), *Salicornia herbecea*, *Salicornia fruiticosa*, and *Salicornia europaea* (Occurring in European countries), are likely to have same activity. So far no compound from *Salicornia brachiata* or from other *Salicornia* species have been reported world over to have anti-tubercular activity. *Salicornia brachiata* plant belonging to Chenopodiaceae family was identified and collected at fully matured stage. The *Salicornia* species is growing in salt marshes of Asia/Africa, Europe and North America.

The present invention therefore provides novel bioactive fractions from crude extracts of Salicornia species. The present invention also relates to a process for the preparation of a plant extract of *Salicornia* species with antitubercular activity which comprises collection of plant at full maturity, washing the plant with using tap water followed by deionised water, removal of all extraneous matter, separation and processing of the plant material to get the desired part, drying, chopping & pulverizing to a certain mesh size, soaking in the solvent & extracting all the soluble matter, concentrating the extract by conventional technique, freeze drying the concentrated extract to get solid residue, fractionating the extract into five fractions using butanol, chloroform, methanol and water, either singly or in combination, testing the crude extract and fractions in-vitro & in-vivo for anti-tubercular activities, specifically against *Mycobacterium tuberculosis* H37Rv, and recording HPLC profiles for the fractions to serve as finger print.

The plant material is preferably washed and dried at a temperature range of 20 to 35° C. until the moisture content is in the range of 0.5 to 1.5 percent The plant material prior to soaking is preferably pulverized and the sieved material in the range of 16-20 mesh size sieve may be selected for further treatment. The extracts and fractions were both tested in-vitro and in-vivo for antitubercular activities.

The plant taxon is an annual, small erect, branched herb, 30-40 cms. in height. It has succulent and articulated stem, opposite branches and short stem internodes. The leaves are reduced to scales, forming a short sheath with rudimentary lamina and sharply pointed tips.

Flowers are trinate, embedded in cavities along with the upper part of the branches. Seed spikes consist of cymes containing three flowers. The middle flower in cymes is noticeably higher than two lateral ones, resulting in at triangular conformation. Stamen one or two, style distinct, stigma subulate, embryo hook both ends pointing downwards. Seeds are erect, compressed, membranous and exalbuminous.

The method of the invention comprises:
1. collecting *Salicornia brachiata* plant material at fully matured stage.
2. washing and drying the plant material at ambient temperature in the range of 25 to 37° C. while maintaining the moisture in the range of 0.5-1.5%.
3. reducing the size of the plant material by pulverizing and selecting the material in the size range of 16-20 mesh sieve.
4. soaking the plant material in deionized water and heated up to 80-90° C. temperature, and repeating the soaking step 5 times with fresh deionized water at an interval of 24 hours.
5. concentrating the extract by conventional/herbal concentrator techniques.
6. freeze drying the concentrated extract in the temperature range of −50 to −60° C. for a period in the range of 8 to 16 hours so as to recover 18-20% yield of crude.
7. fractionating the extract into five fractions F1(5-15% yield) in Butanol, F2 (13-30% yield) in 50% Methanol-Chloroform, F3(34-51% yield) in Methanol, F4(9-15% yield) in 50% Methanol-Water and F5 (3-9% yield) in Water.
8. testing all the five fractions in-vitro and in-vivo for antitubercular activities.
9. sub-fractionating of one of the above active fractions F2 into seven sub-fractions on Semi-preparative HPLC system and testing all the seven sub-fractions for in-vitro anti tubercular activity.
10. purifying the major constituent of the active sub-fraction SF3 on Semi-preparative HPLC system and testing the purified sub-fraction SF3-K for in-vitro & subsequently in-vivo anti tubercular activity.
11. characterizing the purified sub-fraction SF3-K using various spectral analysis for identification of the compound.

According to the present invention, the plant was identified taxonomically and necessary material was collected from the field at fully matured stage. This material was thoroughly washed with deionized water to remove mud, dust particles and foreign matter. The cleaned plant material was dried at room temperature under shade for a period of 3 to 4 weeks. The plant material was pulverized and sieved to obtain 16 to 20-mesh size powder, soaked in deionised water and heated on water bath at 80-90° C. for 5-6 hours. The extraction cycle was repeated for five times using fresh deionised water and filtered under vacuum in Buckner funnel. All the filtrates were then mixed and concentrated using known technique to obtain crude extract. This concentrated extract was freeze dried to obtain moisture-free crude extract in the powder form. This extract was initially tested in-vitro and after several repeated positive tests the extract was further tested for in-vivo antitubercular activity The extract was fractionated in five fractions with solvent mixtures of different polarity and each fraction was tested in-vitro and in-vivo anti tubercular activity. One of the active fractions F2 was sub-fractionated in seven sub-fractions and tested in-vitro and in-vivo anti tubercular activity The active sub-fraction SF3 was purified and obtained SF3-K. The purified sub-fraction SF3-K was tested in-vitro and in-vivo anti tubercular activity and finally subjected for characterization using various spectroscopic methods.

EXAMPLE-1

Wildly growing *Salicornia brachiata* was collected on or before the stage of maturity (November to March) from Gulf of Cambay, India, more precisely from a location at 21° 46' N Latitude & 72° 11' E Longitude to 20 42' N latitude and 71° 01' E longitude (21° 75' N Latitude & 72° 17' E Longitude to 21° 09' N latitude and 72° 00' longitude) as disclosed in U.S. patent application Ser. No. 10/829,400 dated 22$^{nd}$ Apr. 2004 and PCT patent application No. PCT/IN03/00292 dated 29$^{th}$ Aug. 2003. The different parts of the plant were then further processed for crude extract preparation with the solvents: methanol-water (95:5), methanol-water (1:1) at ambient temperature and pure water at 80-90° C. These crude extracts were subjected to bioassay for anti-tubercular activity. The results of bioactivity for many parts found are as under:

| Sr | Plant part | Solvent System | % Mice surviving on Different days |
|---|---|---|---|
| 1 | Root | Methanol-Water (1:1) | 17% up to 28 days |
| 2 | Root | Water (100%) | 17% up to 35 days |
| 3 | Whole Plant without root | Water (100%) | 17% up to 24 days |
| 4 | Seed husk | Methanol-Water (95:5) | 17% up to 23 days |

From the above results it was inferred that the water extract of the root is found containing higher activity than the extract prepared from other plant parts and therefore selected for fractionation work to obtain F1 to F5 fractions as disclosed in the above patent. All the five fractions were evaluated for in-vitro anti tubercular activity and all the fractions found active at 50 µg./mL. Of the above fractions the F2 was selected for further fractionation to obtain the isolated active moiety as further disclosed in the Example 1 of the above patent application. Its activity and HPLC profile were established to be the same (FIG. 1). To improve separation of constituents in the fraction F2, the chromatographic conditions were modified as follows: the mobile phase was 03:97:: $CH_3CN:H_2O$ (isocratic), the column used was 5µ RP-18 analytical column (Phenomenex, U.S.A.), the flow rate was 1 mL/min, the run period was 20 min and the UV detection wavelength was 220 nm. As can be seen from the HPLC profile of FIG. 2, the constituents of the fraction are better resolved.

EXAMPLE-2

1 g. of the F-2 fraction of Example 2 was processed on 10µ RP-18 semi-prep column (Phenomenex, U.S.A.), the flow rate was 6 mL/min, the run period was 28 min and the UV detection wavelength was 220 nm. The HPLC trace is shown in FIG. 3. Subsequently, 50 injections were carried out with a total of 1 g of the F2 fraction and seven sub-fractions (SF-1 to SF-7) were collected as shown in FIG. 3. The sub-fractions were concentrated on rotary evaporator and subsequently freeze dried at −58° C. The weights of the individual sub-fractions were: 238 mg, 312 mg, 160 mg, 5 mg, 9 mg, 1 mg and 8 mg for SF1 to SF7 respectively.

EXAMPLE 3

The sub-fractions SF-1 to SF-7 of Example 2 were tested against *M. tuberculosis* H37Rv in-vitro. The SF3 sub-fraction was consistently found to be active in inhibiting growth and colony forming ability of *M. tuberculosis* H37Rv on 7H10 Middlebrook's medium containing OADC, indicating that the peak shown with an arrow in FIG. 3 is likely the peak corresponding to the most active constituent. (As per the activity flow chart).

EXAMPLE 4

38 mg of the SF-3 sub-fraction of Example 2 was re-chromatographed on the Semi-prep HPLC column maintaining identical conditions as those described in Example 2. Four sub-sub-fractions of this sub-fraction were collected. The third sub-fraction, after stripping off the solvent, weighed 25.3 mg. It yielded the HPLC of FIG. 4 in the Analytical RP-18 column.

EXAMPLE 5

A capped glass vial containing the purified compound of Example-4 was kept for 4 hours around noontime in the hot summer sun to check the thermal stability under Indian weather conditions. The HPLC profile was checked after exposure to the sun and the profile was identical to that of FIG. 4. This demonstrates that the SF3-K has adequate heat stability to withstand storage and transport for the purpose of bioactivity measurements.

EXAMPLE 6

The SF3-K of Example 4 exhibited an MIC value ≦3.125 µg/mL against *M. tuberculosis* H37Rv when evaluated as per the method of Example 3 for which details are provided separately under Bioassay Procedures.

EXAMPLE 7

The in-vitro activity of SF3-K was further determined by another method called BACTEC, for which details are provided separately under Bioassay Procedures. Inhibition of growth of *M. tuberculosis* H37Rv was measured at 50 and 100 µg/mL concentrations. Complete inhibition of growth was observed.

EXAMPLE 8

In a small limited study, the antitubercular activity of SF3-K was evaluated in an experimental model of tuberculosis. The activity of SF3-K was tested at 50 mg per kg body weight in mice infected with *M. tuberculosis* H37Rv. Mice were receiving the purified SF3-K once orally for 12 days. The description and treatment of the two groups is as follows:
Group I Infected, untreated mice
Group II Infected but treated with purified SF3 at 50 mg/kg body weight for 12 days after infection.
The mice in Group I began to loose weight after 10 days following infection. They looked weak with ruffled hairs and mortality began after 14 days of infection. All the mice died of tuberculosis within 16 days. The spleen was enlarged with visible lesion in the lung. All the mice in Group II, which were treated with SF3-K, survived longer and mean survival time was enhanced by 5 days (FIG. 5).

EXAMPLE-9

SF3-K was tested for cytotoxicity (IC50) in VERO cell at different concentrations: 0, 12.5, 25, 50 and 100 µg/mL, The range covers the dose equal to 10 times the MIC of SF-3 for *M. tuberculosis* H37Rv. After 72 hours exposure, viability was assessed on the basis of cellular conversion of MTT into a formazan product (using the Promega CellTitre 96 non-radioactive Cell Proliferation Assay), which was measured by absorbance at 492 nm. There was no inhibition up to 100 µg/mL, suggesting that the compound was non-cytotoxic. The result is shown in FIG. 6. Two cytotoxic compounds designated X and Y were taken for comparison.

EXAMPLE-10

Toxicity studies were also conducted on healthy mice treated with SF3-K. Seven mice were given once daily (by oral route) a dose of SF3-K amounting to 50 mg/kg of body weight for 12 continuous days and observed for survival and weight till 35 days. None of the mice died and they gained weight.

EXAMPLE-11

The TOCSY (Total Correlation Spectroscopy) proton NMR spectrum of SF3-K was recorded on a 500 MHz Varian NMR machine (FIG. 7). Except for the circled peaks, all other peaks are attributable to sucrose and separate NMR experiments with pure sucrose (Sigma) have confirmed this. Based upon HPLC with RI detection, the approximate percentage of Sucrose in SF3-K is 75-80%, indicating thereby that the minor constituents comprise no more than 20-25%. Further based on comparative $^1$H NMR of SF3-K and standard Sucrose (Sigma) having equal quantity of weight indicates approximately 5% difference in the proton signal area. Similarly, in minor constituents the ratio between the compounds with molecular weight 117 and 142 is approximately 4:1 based upon HPLC with UV detection This example illustrates that SF3-K is primarily sucrose with presence of one or more minor constituents responsible for the circled peaks.

EXAMPLE-12

Experiments were conducted with control, pure sucrose from Sigma (100 µg/mL) and SF3-K (50 µg/mL) in-vitro against H37Rv using the BACTEC method. As can be seen from FIG. 8 no inhibition was observed with sucrose and the behaviour was similar to that found with control, whereas SF3-K showed significant inhibition. If Sucrose plays no role other than being a diluent, the MIC value of the active constituent(s) in SF3-K would be expected to be much lower than the value indicated in Example 6 since the active constituents comprise no more than 20-25% in SF3-K as indicated in Example 11.

EXAMPLE-13

The experiment of Example 12 was repeated at two different dose levels of SF3-K, namely 50 µg/mL and 100 µg/mL. As can be seen from FIG. 9, the observations of Example 12 were found to be reproducible (FIG. 9). Moreover, dose dependence of inhibition was seen.

EXAMPLE-14

The HPLC conditions of Example 1 using 03:97::CH$_3$CN:H$_2$O was repeated with pure Sucrose and no peak was found in the chromatogram under 220 nm detection whereas RI detection revealed a peak with similar retention time as that of SF3-K under 220 nm UV detection or under RI detection. No other peaks due to any minor constituent were observed either by UV detection or by RI detection of the SF3-K. This example suggests that minor constituents in SF3-K, whose presence is evident from the TOCSY NMR of Example 11 and the activity data of Examples 12 and 13, co-elute with sucrose under the chromatographic conditions adopted.

EXAMPLE-15

The HPLC conditions were modified to resolve the constituents of SF3-K having the chromatogram of FIG. 4 under the prior conditions of HPLC. For this the following changes were made The RP-18 column was replaced with a Waters Amino column and the mobile phase was changed to 80:20::CH$_3$CN:H$_2$O. The chromatogram obtained (210 nm detection) under LC-MS run conditions is shown in FIG. 10. As can be seen from the figure, peaks were obtained at 3.09 min, 4.26 min, 15.92 min, and 20.74 min. Separate experiments with pure Sucrose (Sigma) under the same conditions using RI detection revealed a peak at 7.70 min, i.e., Sucrose elutes at 7.70 min but goes undetected in UV. Accordingly, mass spectral characterization was attempted of the constituents eluting at 4.26 min, 7.70 min, 15.92 min, and 20.74 min (FIGS. 11 A-D). The mass spectrum (scan ES$^+$) of SF3-K as such is shown in FIG. 12. The constituent eluting at 4.26 min shows m/z=114 corresponding to [113+H]$^+$, i.e., it has the molecular weight of 113. Under MS conditions, the compound also forms the dimeric aggregate [(113)$_2$+H]$^+$ having peak at m/z=227. The constituent eluting at 7.70 min (FIG. 11B) has m/z=360 corresponding to [Sucrose (342)+NH$_4^+$(18)], i.e., it is due to Sucrose as expected. The constituent eluting at 15.92 min (FIG. 11 C) shows the MS peak at m/z=118 corresponding to [117+H]$^+$, i.e., it has the molecular weight of 117. Under MS conditions, the compound also forms dimeric [(117)$_2$+H]$^+$ and trimeric [(117)$_3$+H]$^+$ clusters having m/z=235 and 352, respectively. MS-MS showing the daughter peaks of the m/z=118 [117+H]$^+$ and 140 (1.17+Na$^+$) in the spectrum of FIG. 12 are shown in FIGS. 13a & b. Based on the fragmentation pattern of FIGS. 13a & b, NMR positions of "non-Sucrose" circled peaks in FIG. 7, and IR evidence of amide and carbonyl bands for SF3-K (FIG. 14a) not seen with sucrose (FIG. 14b) the structure (1) below could be one of the possible structures corresponding to m/z=118 (this constituent appears to be dominant among the "minor constituents" of SF3-K). The constituent eluting at 20.74 min (FIG. 11D) shows the m/z at 143 [142+H$^+$] but has not been characterized further. Besides these peaks, a peak at m/z=116 [115+H]$^+$ has been observed as also a peak at m/z=138 [115+Na$^+$] both under direct spray of SF3-K as also as co-constituent of m/z=118 during LC-MS. The complex pattern of the mass spectrum of FIG. 12 can be explained in terms of clusters of Sucrose either with itself or with the minor constituent having molecular weight of 117.

Methods

Preparation of SF3-K from Dry Mature Root of *Salicornia Brachiata*

*Salicornia brachiata* was collected at fully matured stage and the roots were used preparation of aqueous extract as disclosed in the pending U.S. patent application Ser. No. 10/829,400 dated 22$^{nd}$ Apr. 2004 and PCT patent application No. PCT/IN03100292 dated 29$^{th}$ Aug. 2003 by Rathod et al. The root was washed with tap water followed by deionized water to remove mud, dust particles and other foreign matter, dried, cut to small pieces, pulverized and soaked in the deionized water. The soaked root was heated on water bath at 80-90° C. The water-soluble extract was decanted and filtered. The above process was carried out for three to five days so as to recover au the water-soluble material. The filtrate was concentrated on a rotary evaporator and subsequently dried on Freeze Drier to obtain a solid. The solid was fractionated to obtain five fractions through successive extraction with Butanol, 1:1 Chloroform:Methanol, Methanol, 1:1 Methanol:Water and Water. The Chloroform:Methanol fraction (referred to as F2) was taken for sub-fractionation on Semi-preparative HPLC using RP-18 column (Phenomenex) and 03:97::CH$_3$CN:H$_2$O mobile phase at 7 mL/min. Seven sub-fractions were collected between 0 to 22 minutes and the sub-fraction collected between 9.9 minutes and 10.65 minutes was labeled as SF3 The SF3 was concentrated on rotary evaporator at 50° C. and then subjected to chromatography once again on the same column and under the same conditions except for change of flow rate to 6 mL/min and total run period of 19 minutes. The fraction corresponding to the main peak was collected between 11.8 to 12.6 minutes, i.e., the collection began during the rising phase of the peak above baseline and was discontinued during the declining phase of the peak but before reaching baseline. This sub-fraction was once again concentrated on rotary evaporator and freeze dried to obtain a powder. Starting with 100 g of dry root 0.805 g of SF3-K was obtained.

In-Vitro Screening of SF3-K against *M. Tuberculosis* H37Rv Using 7H10 Middlebrook's Medium Containing OADC (B-D, USA).

The antitubercular activity of SF3-K was determined by inhibition of growth and colony forming ability of *M, tuberculosis* H37Rv on 7H10 Middlebrook's medium containing OADC (B-D, USA). The medium was autoclaved and supplemented with OADC and 2 mL was dispensed in sterile tubes. A suspension of 1 mg/mL. concentration of SF3-K fraction was prepared in sterile water, which was added into test tubes containing supplemented medium at different concentrations keeping the volume constant, i.e. 0.1 mL. After proper mixing, the tubes were kept in slanting position and allowed to cool and solidity. These tubes were incubated at 37° C. for 24 hours to observe any contamination. If not, the tubes were streaked with a culture suspension of *M. tuberculosis* H37Rv ($1-5 \times 10^4$ bacilli/tube). The inoculated tubes were incubated at 37° C. along with two controls, one in which no inhibitory compound was present but streaked with the same inoculum of *M. tuberculosis* H37Rv and second, in which a standard antitubercular compound was added at the reported minimum inhibitory concentration which will inhibit the growth of tubercle bacilli. Growth of bacilli was observed till 4 weeks of incubation. SF3-K containing tubes were compared with control tubes described above.

BACTEC Method of In-Vitro Screening:

Aqueous stock solution of SF3-K (1 mg/mL) was filter sterilized. 50 μL of SF3-K was added to 4 mL radiometric 7H12 broth (BACTEC 12B) to achieve final concentration of 50 and 100 μg/mL of SF3-K. 50 μL sterile water was added in the control vial in which SF3-K was not added. Finally, $10^4$ to $10^5$ colony forming units of *M. tuberculosis* H37Rv was inoculated in all the vials, that is, the 4 mL. BACTEC radiometric 7H12 broth containing 50 and 100 μg/mL of SF3-K and the control vial without SF3-K. All the vials were kept in duplicate and incubated at 37° C. Growth index (GI) was recorded daily. Experiments were done in analogous fashion with Sucrose (Sigma; 100 μg/mL) instead of SF3-K to ascertain its activity, if any.

Method of In-Vivo Screening.

*M. tuberculosis* H37Rv, grown on L-J slants, was harvested and a homogenous Suspension was prepared in Tween-saline at approximately $1 \times 10^8$ bacilli/mL. Female swiss mice, bred in the animal house of Central Drug Research Institute, Lucknow, India and weighing 18-20 g were taken. The mice were divided in 2 groups with 7 mice in each group. Infection of mice with *M. tuberculosis* H37Rv ($1 \times 10^7$ bacilli/mouse) was given by injecting 0.1 mL of the bacterial suspension as prepared and described above via lateral tail vein. Treatment of mice with SF3-K (50 mg/kg body weight, dissolved in sterile water) was started after 48 hours post infection and administered via oral route for 12 days.

The main inventive steps are:
(i) changing the chromatographic condition that enabled purification of F2.
(ii) Correlating the sub-fractions of F2 with activity and selecting SF3 for further study.
(iii) Further purifying SF3 to obtain SF3-K that yielded a single peak in the HPLC that suggested apparent high purity.
(iv) Identifying sucrose as major constituent of SF3-K and further demonstrating that it is inactive.
(v) Showing thereafter that sucrose elutes at the same place as where UV-responsive peaks are detected, where these peaks are likely due to minor constituents.
(vi) Proving by 2D-NMR that additional NMR peaks other than for Sucrose are due to minor constituents and not due to functional modification of Sucrose.
(vii) Evolving methodology for separating the various constituents of SF3-K and attempting preliminary characterization.
(viii) Indirectly demonstrating that the <3.125 μg/mL MIC of SF3-K translates into a very low MIC of active minor constituents which therefore need to be isolated and studied separately.
(ix) Showing that the SF3-K is completely non-toxic.
(x) Demonstrating efficacy of action both in-vitro and in-vivo The Main Advantages of the Present Invention are:
Reduction in the MIC value of anti-tubercular extract from *Salicornia brachiata* through concentration of activity in a specific sub-fraction named SF3-K, leading to MIC values $\leq 3.125$ μm/mL.
2. Proven efficacy of anti-tubercular action in-vivo through limited studies on mice infected with H37Rv as demonstrated through enhanced survival period.
3 Proven non-toxic nature of the sub-fraction through cytotoxicity studies conducted with dosage well above ten times the MIC value.
4. Mirroring of the same non-toxic behaviour in healthy mice administered with the active
5 Adequate thermal and photochemical stability of SF3-K as demonstrated through exposure of the solid to mid-noon Indian sun that led to no change in HPLC profile with UV detection.
6. Reproducibility of activity through repeat collections of the plant and repeat extraction and fractionation.
7 Demonstration that activity of SF3-K resides in minor constituents and thereby holding out the promise of achieving further 3 to 5 fold reduction in the MIC value by isolating the active constituent free from the major inactive constituent, namely Sucrose.
8 Demonstration of the feasibility of separating the minor constituents of SF3-K from the major inert constituent by chromatographic means which would make possible a detailed study of the anti-TB activity of the different minor constituents of SF3-K with a view to identify the key active ingredient and synergy of action, if any, with other constituents of SF3-K or even with other known drugs currently in vogue or to be introduced soon.
9. Demonstration that the minor constituent(s) of SF3-K, one or more of which are active against *M. tuberculosis*, are simple molecule(s) based on mass spectral data and possibly not investigated previously for anti-tubercular activity.
10 Possibility that the SF3-K may be used as a novel, non-toxic and efficacious herbal drug against *M. Tuberculosis* once detailed tests from all angles are completed.
11. Possibility that SF3-K may yield a new chemical entity against *M. Tuberculosis* that may be amenable to synthesis as well.
12. So far the known compounds of tuberculosis are found having complex structure and heterocyclic. Where as the compound isolated in present investigation appears to be very simple, and having low molecular weight (117).

We claim:
1. A bioactive sub-fraction SF3-K with anti-tubercular activity isolated from a Chloroform-Methanol (1:1) fraction F2 of a water extract of *Salicornia brachiata* roots.
2. The bioactive sub-fraction SF3-K as claimed in claim 1, wherein SF3-K is prepared from the F2 fraction, a Chloroform-Methanol (1:1) fraction of an aqueous crude extract from *Salicornia brachiata* roots, comprising the following steps:
(i) providing F2 fraction from *Salicornia brachiata*;
(ii) subjecting the F2 fraction to sub-fractionation on a semi-preparative HPLC using a RP-18 column and $CH_3CN:H_2O$ (03:97) as a mobile phase at a flow rate of 7 mL/min;

(iii) collecting seven sub-fractions SF1, SF2, SF3, SF4, SF5, SF6 and SF7 between 0 to 22 minutes of the semi-preparative HPLC;

(iv) subjecting the sub-fractions obtained in step (iii) to anti-tubercular screening;

(v) identifying the sub-fraction SF3 with anti-tubercular activity;

(vi) concentrating the sub-fraction obtained in step (v) and re-chromatographing on the semi-preparative column using the same conditions except at a flow rate of 6 mL/min to enhance the purity of a peak having a retention time of 11.89 min at 6 mL/min flow rate on a semi-preparative column;

(vii) concentrating the sub-fraction obtained in step (vi) and subjecting to freeze drying to obtain SF3-K.

3. The bioactive sub-fraction SF3-K as claimed in claim 2 wherein the sub-fraction obtained in step (vi) is subjected to freeze drying to obtain solid SF3-K in 0.6 to 0.9% yield based on the dry weight of root.

4. The bioactive sub-fraction SF3-K as claimed in claim 1, wherein the SF3-K is stable at least for 4 hours at a temperature of up to 50° C.

5. The bioactive sub-fraction SF3-K as claimed in claim 1, wherein the bioactive sub-fraction SF3-K exhibits an MIC value of less than or equal to 3.125 µg/mL against *M. tuberculosis* H37Rv when evaluated using 7H10 Middlebrook's medium containing OADC (Oleic acid-Albumin-Dextrose-Catalase).

6. The bioactive sub-fraction SF3-K as claimed in claim 1, wherein the bioactive sub-fraction SF3-K exhibits dose-dependent inhibition against *M. tuberculosis* H37Rv in vitro at dosages between 50 µg/mL and 100 µg/mL.

7. The bioactive sub-fraction SF3-K as claimed in claim 1, wherein the sub-fraction SF3-K increases the mean survival time (MST) of infected mice at an oral dosage of 50 mg/kg of body weight.

8. The bioactive sub-fraction SF3-K as claimed in claim 1, wherein the sub-fraction SF3-K exhibits no cytotoxicity in a test conducted with a VERO cell line even at a dosage up to 100 µg/mL, which is more than beyond ten times of the MIC value of SF3-K.

9. The bioactive sub-fraction SF3-K as claimed in claim 1, wherein the sub-fraction SF3-K exhibits no toxicity towards healthy mice when administered orally at a dosage up to 50 mg/kg of body weight.

10. The bioactive sub-fraction SF3-K as claimed in claim 1, wherein the major constituent of SF3-K comprises 75 to 80% sucrose based on HPLC analysis.

11. The bioactive sub-fraction SF3-K as claimed in claim 1, wherein the major constituent sucrose does not have any anti-tubercular activity at a dosage of 100 µg/mL.

12. The bioactive sub-fraction SF3-K as claimed in claim 1, wherein the most prominent minor constituent exhibits m/z values of 118[117+H$^+$] and 140 [117+Na$^+$] corresponding to a molecular weight of the constituent of 117.

13. The bioactive sub-fraction SF3-K as claimed in claim 1, wherein the most prominent minor constituent having a molecular weight of 117 shows daughter peaks corresponding to m/z values of 58 and 59 whereas daughter fragments in the form of sodium salt have m/z values of 96, 81, 53, and 23.

14. The bioactive sub-fraction SF3-K as claimed in claim 1, wherein the most prominent minor constituent having a molecular weight of 117 forms self-clusters under the conditions of mass spectroscopy and also forms clusters with the major constituent sucrose.

15. The bioactive sub-fraction SF3-K as claimed in claim 12, wherein other minor constituents have molecular weights of 113, 115 and 142.

16. The bioactive sub-fraction SF3-K as claimed in claim 2, wherein the sub-fractions SF1, SF5, SF6 and SF7 have anti-tubercular activity at 12.5-100 µg/mL and SF2 and SF4 have anti-tubercular activity at 25-100 µg/mL.

17. A method for treatment of tuberculosis comprising administering to a subject in need thereof, a pharmaceutically effective amount of an anti-tubercular sub-fraction SF3-K obtained from fraction F2, a Chloroform-Methanol (1:1) fraction of a water extract of *Salicornia brachiata* roots, optionally along with any other anti-tubercular drug of synthetic or natural origin and a pharmaceutically acceptable additive or carrier.

18. The method as claimed in claim 17, wherein the fraction F2, a Chloroform-Methanol (1:1) fraction, is sub-fractionated into SF1, SF2, SF3, SF4, SF5, SF6 and SF7.

19. The method as claimed in claim 17, wherein the major constituent of SF3-K comprises 75 to 80% sucrose based on HPLC analysis.

20. The method as claimed in claim 17, wherein the sub-fraction SF3-K exhibits a MIC value less than or equal to 3.125 µg/ML against *M. tuberculosis* H37Rv when evaluated using 7H10 Middlebrook's medium containing OADC (Oleic acid-Albumin-Dextrose-Catalase).

21. The method as claimed in claim 17, wherein the sub-fraction SF3-K exhibits dose-dependent inhibition against *M. tuberculosis* H37Rv at dosages between 50 µg/mL and 100 µg/mL.

22. The method as claimed in claim 17, wherein the sub-fraction SF3-K increases the mean survival time (MST) of infected mice at an oral dosage of 50 mg/kg of body weight.

23. The method as claimed in claim 17, wherein the sub-fraction SF3-K exhibits no cytotoxicity a test conducted with a VERO cell line even at a dosage up to 100 µg/mL, which is more than ten times of the MIC value of SF3-K.

24. The method as claimed in claim 17, wherein the sub-fraction SF3-K does not show toxicity towards healthy mice when administered orally at a dosage up to 50 mg/kg of body weight.

25. The method as claimed in claim 19, wherein the major constituent sucrose does not have any anti-tubercular activity when tested at a dosage of 100 µg/mL.

26. The method as claimed in claim 17, wherein the most prominent minor constituent SF3-K exhibits m/z values of 118[117+H$^+$] and 140 [117+Na$^+$] corresponding to a molecular weight of the constituent of 117.

27. The method as claimed in claim 17, wherein the most prominent minor constituent SF3-K having a molecular weight of 117 shows daughter peaks corresponding to m/z values of 58 and 59 whereas daughter fragments in the form of sodium salt have m/z values of 96, 81, 53, and 23.

28. The method as claimed in claim 17, wherein the most prominent minor constituent SF3-K having a molecular weight of 117 forms self-clusters under the conditions of mass spectroscopy and also forms clusters with the major constituent sucrose.

29. The method as claimed in claim 26, wherein other minor constituents SF3-K are observed with molecular weights of 113, 115 and 142.

30. The method as claimed in claim 18, wherein the sub fractions SF1, SF5, SF6 and SF7 have anti-tubercular activity at 12.5-100 µg/mL and SF2 and SF4 have anti-tubercular activity at 25-100 µg/mL.

31. The method as claimed in claim 17, wherein the sub-fraction SF3-K is administered in a form selected from the group consisting of tablets, lozenges, capsules, powder, solution, intravenous dosage and oral dosage.

* * * * *